United States Patent
Osinski et al.

(10) Patent No.: US 6,984,744 B2
(45) Date of Patent: Jan. 10, 2006

(54) PHOSPHINE LIGANDS

(75) Inventors: Piotr Osinski, Nowy Dwor Mazowiecki (PL); Kazimierz Michal Pietrusiewicz, Lublin (PL); Rudolf Schmid, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 137 days.

(21) Appl. No.: 10/721,038

(22) Filed: Nov. 21, 2003

(65) Prior Publication Data

US 2004/0110975 A1 Jun. 10, 2004

(30) Foreign Application Priority Data

Nov. 29, 2002 (EP) ............................................ 02026831

(51) Int. Cl.
  *C07F 15/00* (2006.01)
  *C07F 9/02* (2006.01)
  *C23C 37/00* (2006.01)
  *C07C 5/03* (2006.01)

(52) U.S. Cl. ............................ 556/21; 568/12; 568/17; 568/799; 568/814; 585/277

(58) Field of Classification Search ................... 556/21; 556/568/12, 17, 799, 814; 585/277
See application file for complete search history.

(56) References Cited

U.S. PATENT DOCUMENTS

2003/0144137 A1 * 7/2003 Zhang et al. ................ 502/162

FOREIGN PATENT DOCUMENTS

JP     2002069086    *  3/2002

OTHER PUBLICATIONS

Cremer et al., J. Org. Chem., 36, pp. 3226–3231 (1971).
Tang et al., Angew. Int. Ed., 41, pp. 1612–1614 (2002).
Burk et al., Tetrahedron Asymmetry, 2, pp. 569–592 (1991).
Fryzuk et al., J. Am. Chem. Soc., 99, pp. 6262–6267 (1977).
Fryzuk et al., J. Am. Chem. Soc., 100, pp. 5491–5494 (1978).
Mroz et al., Molecular Physics Reports, 29, pp. 205–209 (2000).

* cited by examiner

*Primary Examiner*—Porfirio Nazario-Gonzalez
(74) *Attorney, Agent, or Firm*—George W. Johnston; Patricia S. Rocha-Tramaloni; David E. Wildman

(57) ABSTRACT

The invention is concerned with new phosphine ligands of formula I

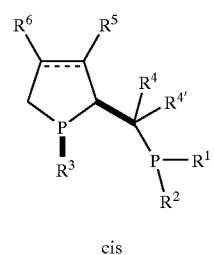

cis wherein
$R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl; $R^3$ is alkyl, cycloalkyl, aryl or heteroaryl; $R^{4'}$ and $R^4$ are independently of each other hydrogen, alkyl or optionally substituted aryl; or $R^{4'}$ and $R^4$ together with the C-atom they are attached, form a 3–8-membered carbocyclic ring; dotted line is optionally a double bond; $R^5$ and $R^6$ are independently of each other hydrogen, alkyl or aryl, $R^7$ is alkyl or aryl; and $R^8$ and $R^{8'}$ are independently of each other hydrogen, alkyl or aryl; the substituents attached by the bold bonds are in cis relation to each other; metal complexes with such ligands in asymmetric reactions.

27 Claims, No Drawings

PHOSPHINE LIGANDS

FIELD OF THE INVENTION

The present invention is related to new phosphine ligands, metal complexes of such ligands, as well as the use of such metal complexes as catalysts in asymmetric reactions.

BACKGROUND OF THE INVENTION

Phosphine ligands with chiral centers on carbon and phosphorous atoms are known in the art. A particular class of phosphine ligands are those linked by a bridge of two carbon atoms, i.e., 1,2-diphosphine ligands. Examples of 1,2-diphosphine ligands with one or two chiral centers on the carbon atoms of the bridge are PROPHOS (A) as described in *J. Am. Chem. Soc.* 1978, 100, 5491; and CHIRAPHOS (B) see *J. Am. Chem. Soc.* 1977, 99, 6262. Another type of 1,2-diphosphine ligands are those where the chiral center is on C atoms in a phospholane ring such as for example in the BPE ligand (C), described in *Tetrahedron Asymmetry*, 1991, 2,(7), 569. Still another type of 1,2-diphosphine ligands are those where the chiral centers are on the C and P atoms such as in compound D, described in *Angew. Chem. Int. Ed.* 2002, 41(9), 1612.

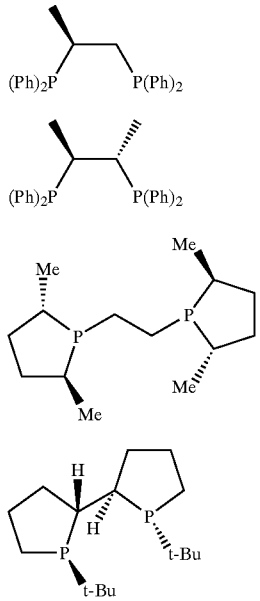

SUMMARY OF THE INVENTION

The present invention provides a new phosphine ligands of the formula I

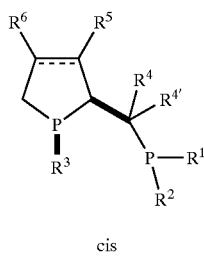

wherein
$R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —$SO_2$—$R^7$, —$SO_3^-$, —CO—$NR^8R^{8'}$, carboxy, alkoxycarbonyl, trialkylsilyl, diarylalkylsilyl, dialkylarylsilyl or triarylsilyl;
$R^3$ is alkyl, cycloalkyl, aryl or heteroaryl;
$R^{4'}$ and $R^4$ are independently of each other hydrogen, alkyl, aryl or substituted aryl; or
$R^{4'}$ and $R^4$ together, with the C-atom they are attached, form a 3–8-membered carbocyclic ring;
dotted line is optionally a double bond;
$R^5$ and $R^6$ are independently of each other hydrogen, alkyl or aryl;
$R^7$ is alkyl, aryl or $NR^8R^{8'}$; and
$R^8$ and $R^{8'}$ are independently of each other hydrogen, alkyl or aryl;
the substituents $R^3$ on the phospholane phophorus atom and the substituent on the C2 atom of the phospholane ring being in cis relation to each other as indicated by the bold bonds in formula I.

The residues $R^4$, $R^{4'}$, $R^5$ and $R^6$ may form additional chiral centers on the C atom they are attached to and the residues $R^1$ and $R^2$ may form an additional chiral center on the phosphorus atom they are attached to.

The present invention is also directed to chiral 1,2-diphosphine ligands with one chiral center on a carbon atom of the bridge and one chiral center on the phosphorous atom, i.e., a new bidenate C,P-chiral 1,2-diphosphine ligand system which form fairly rigid bicycle[3.3.0]octane chelates with transition metals.

DETAILED DESCRIPTION OF THE INVENTION

The following definitions of the general terms used in the present description apply irrespective of whether the terms in question appear alone or in combination.

The term "alkyl" as used herein signifies straight-chain or branched hydrocarbon groups with 1 to 8 carbon atoms, preferably 1 to 6 carbon atoms, such as methyl, ethyl, propyl, iso-propyl, butyl, iso-butyl and tert.-butyl. Preferably the alkyl groups for $R^1$, $R^2$ and $R^3$ are branched alkyl groups such as iso-propyl, iso-butyl and tert.-butyl.

The term "alkoxy" denotes a group wherein the alkyl residue is as defined above, and which is attached via an oxygen atom.

The term "cydoalkyl" stands for 3- to 8-membered rings, such as cyclopropyl, cyclobutyl, cyclopentyl, cyclohexyl and cycloheptyl, especially for cyclopentyl or cyclohexyl. Unless otherwise stated, said "alkyl" and "cycloalkyl" groups may be substituted by alkyl (for cycloalkyl), alkoxy, halogen, hydroxy, amino, mono- or dialkylamino, or aryl.

The term "aryl" signifies an aromatic hydrocarbon residue, especially the phenyl residue, which can be unsubstituted or substituted in the ortho-, meta- or para-position or multiply-substituted. Substituents which come into consideration are e.g. phenyl, alkyl or alkoxy groups, preferably methyl or methoxy groups, or amino, monoalkyl- or dialkylamino, preferably dimethylamino or diethylamino, or hydroxy, or halogen such as chlorine, or trialkylsilyl, such as trimethylsilyl. Moreover, the term "aryl" can signify naphthyl. Preferred aryl residues are phenyl, tolyl, dimethylphenyl, di-tert.-butylphenyl or anisyl.

The term "heteroaryl" signifies a 5- or 6-membered aromatic cycle containing one or more heteroatoms such as S, O and/or N. Examples of such heteroaryl groups are furyl, thienyl, benzofuranyl or benzothienyl.

The compounds of the invention have two chiral centers, one on the P atom in the phospholane ring and one on the C2 atom of the phospholane ring. The substituents at these chiral centers are always in cis relation to each other.

For the denotation of cis- and trans configuration in the compounds of the invention and of related compounds the convention depicted below is adhered to:

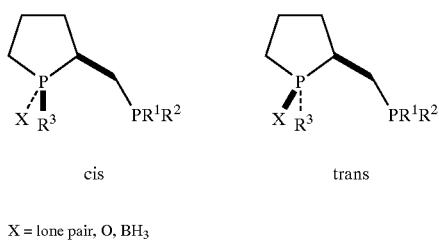

X = lone pair, O, BH$_3$

Compound of formula Ia is an example of a compound of formula I, wherein $R^5$ and $R^6$ are independently of each other hydrogen, alkyl or aryl, and the dotted line is present and forms a double bond:

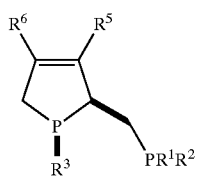

Ia

Preferred compounds of formula I are those wherein
$R^1$ and $R^2$ are the same and are unsubstituted alkyl, aryl, cycloalkyl or heteroaryl, or alkyl, aryl, cycloalkyl or heteroaryl each of which is independently substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;
$R^3$ is alkyl or aryl;
$R^{4'}$ and $R^4$ are hydrogen;
$R^5$ and $R^6$ are independently of each other hydrogen, C$_1$–C$_3$-alkyl or phenyl;
the dotted line is absent;
$R^7$ is alkyl, aryl or NR$^8$R$^{8'}$; and
$R^8$ and $R^{8'}$ are independently of each other hydrogen, alkyl or aryl;
the substituents $R^3$ on the phospholane phophorus atom and the substituent on the C2 atom of the phospholane ring being in cis relation to each other as indicated by the bold bonds in formula I.

One embodiment of the invention is compounds of formula I wherein
$R^1$ and $R^2$ are the same and are aryl;
$R^3$ is tert.-butyl or phenyl;
$R^{4'}$ and $R^4$ are identical and signify hydrogen;
$R^5$ and $R^6$ are hydrogen; and the dotted line is absent.

Another embodiment is compounds of formula I wherein
$R^1$ and $R^2$ are the same and are alkyl;
$R^3$ is tert.-butyl or phenyl;
$R^{4'}$ and $R^4$ are the same and are hydrogen;
$R^5$ and $R^6$ are hydrogen; and the dotted line is absent.

Another embodiment is compounds of formula I wherein
$R^1$ and $R^2$ are the same and are cycloalkyl;
$R^3$ is tert.-butyl or phenyl;
$R^{4'}$ and $R^4$ are the same and are hydrogen;
$R^5$ and $R^6$ are hydrogen; and the dotted line is absent.

A further embodiment is compounds of formula I wherein
$R^1$ and $R^2$ are alike and signify heteroaryl;
$R^3$ is tert.-butyl or phenyl;
$R^{4'}$ and $R^4$ are identical and signify hydrogen;
$R^5$ and $R^6$ are hydrogen; and the dotted line is absent.

Especially preferred ligands of formula I are those wherein $R^1$ and $R^2$ are the same and are phenyl, $R^3$ is phenyl and $R^4$, $R^{4'}$, $R^5$ and $R^6$ are hydrogen.

The ligands of formula I are prepared according to the reaction scheme 1 to 3. The starting materials are known in the art and commercially available.

The synthesis of 2-methylenephospholane-1-oxide is carried out according to scheme 1 starting from the appropriately substituted phospholane-1-oxide (1) which may be prepared in analogy to the method described for 1-phenylphospholane-1-oxide in *J. Org. Chem.* 1971, 36, 3226.

In the generic formulae of the schemes (R)- and (S)-configurational assignments of the phospholane phosphorus atom are based on the Cahn-Ingold-Prelog rules with an arbitrarily chosen priority of $R^3$>C2 of phospholane ring>C5 of phospholane ring.

Scheme 1

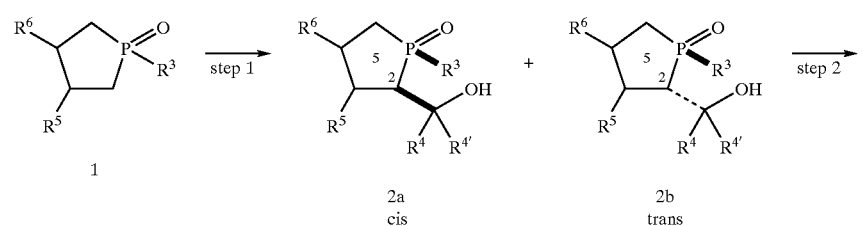

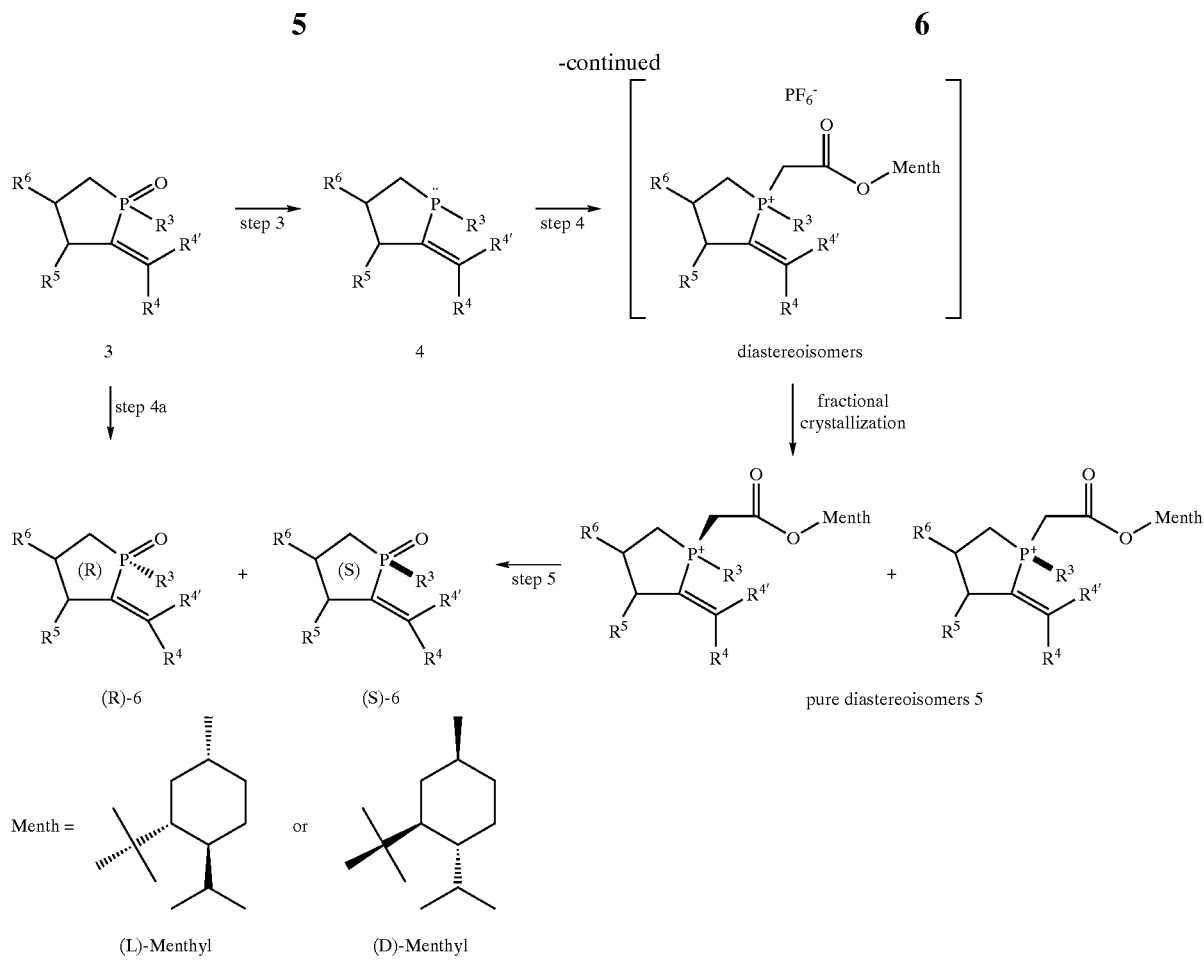

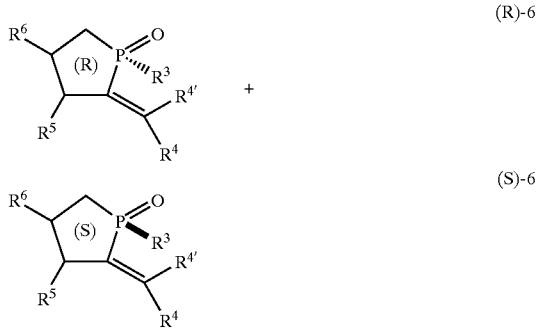

(L)-Menthyl    (D)-Menthyl wherein the residues are as defined above for formula I.

The optical active intermediates of formula 6 wherein $R^3$, $R^4$, $R^{4'}$, $R^5$ and $R^6$ are as defined for formula I above; are new and thus part of the present invention.

Step 1

The phospholane 1-oxide (1) is metallated with a metallation reagent, such as an aryl or alkyl lithium reagent or a lithium amide reagent and subsequently reacted with an aldehyde such as e.g., formaldehyde or a ketone such as e.g., acetone to yield mixtures of cis- and trans-2-phospholanemethanol 1-oxide (2a and 2b). Metallation reagents may be phenyl-, butyl-, sec- and tert.-butyllithium or the like, or lithium-di-iso-propylamide, lithium-2,2,6,6-tetramethylpiperidide or the like. In a preferred version an aryl or alkyl lithium reagent is used which contains the aryl or alkyl group $R^3$.

Step 2

2-Methylene-oxo-phospholane (3) is formed by dehydration of cis- or trans 2-phospholanemethanol 1-oxide (2a and b) or of mixtures thereof. Such dehydration can be performed by methods known to the person skilled in the art. For example, the dehydration can be performed by reaction of the hydroxy group with an inorganic acid chloride such as thionylchloride or phosphoroxichloride and subsequent elimination of the formed chloride intermediate, for example, in presence of an organic base such as 1,8-diazabicyclo[5.4.0]undec-7-ene (DBU), 1,5-diazabicyclo[4.3.0]non-5-ene (DBN), 1,4-diazabicyclo[2.2.2]octane (DABCO), triethylamine or pyridine or the like. In another method the dehydration is performed by catalysis with a strong acid such as e.g., sulfuric acid, phosphoric acid, pyrophosphoric acid, potassium hydrogen sulfate, p-toluenesulfonic acid, etc. In still another method an ester derived from an organic acid such as methanesulfonic acid or p-toluenesulfonic acid is formed and the subsequent elimination performed with an organic base such as 1,8-diazabicyclo[5.4.0]undec-7-ene, triethylamine or pyridine or the like. In yet another method, an ester derived from acetic acid is formed and subjected to pyrolytic elimination.

Step 3

2-Methylenephospholane-1-oxide (3) is reduced to the corresponding phospholane (4) by methods known in the art. Such reduction can be achieved, for example, by treatment with silane reagents (e.g., trichlorosilane, hexachlorodisilane, phenylsilane, polymethylhydrosiloxane, etc.), aluminum reagents (e.g., lithium or natrium aluminum hydride, aluminum hydride), metals (aluminum, magnesium) or with hydrogen after activation with phosgene.

Steps 4 and 5

On the one hand optical resolution of 2-methylenephospholane (4) by quaternisation reaction with an optically active alkylating agent such as, for example, with (L)- or (D)-methyl-2-bromo-acetate and fractional crystallization of the salt yields the diastereomerically pure methyl acetate derivatives (5), which then are cleaved in the presence of a base such as sodium hydroxide to the enantiomerically pure 2-methylene-1-oxo-phospholanes (6).

Step 4a

On the other hand 2-methylene-1-oxo-phospholane (3) can be separated into the enantiomerically pure 2-methylene-1-oxo-phospholanes (6) by chromatography on a chiral support.

Step 6

The enantiomerically pure 2-methylenephospholane-1-oxides (6) are transformed into a mixture of the corresponding cis- and trans-bisoxides (7) according to scheme 2.

Scheme 2

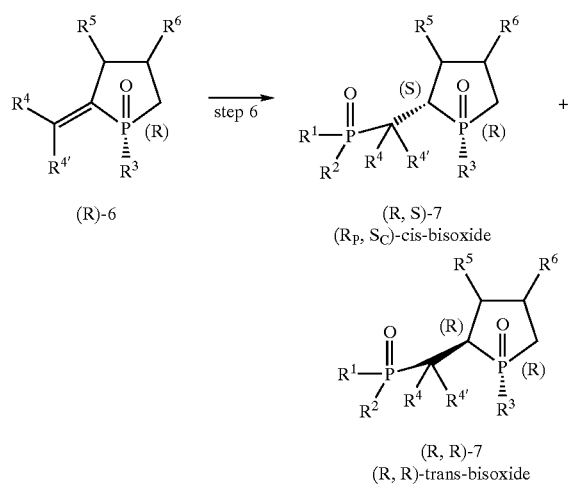

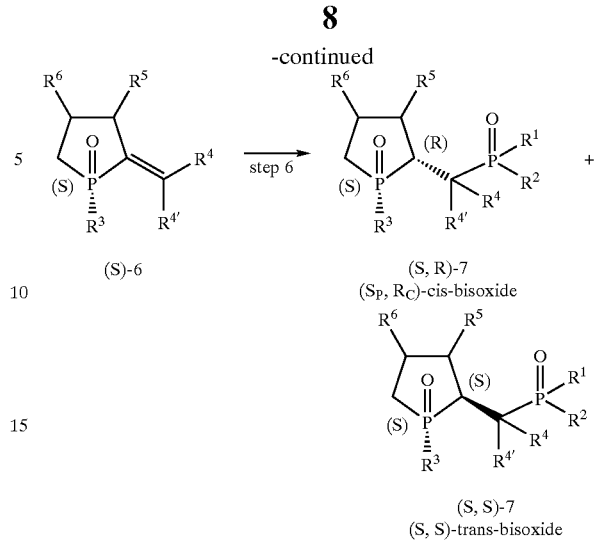

wherein the residues are as defined above for formula I.

The transformation is performed by adding a secondary phosphine oxide which can proceed under purely thermal conditions by heating or under base catalysis conditions, e.g., with amine bases such as 1,8-diazabicylclo[5.4.0] undec-7-ene (DBU), 1,5-diazabicyclo[4.3.0] non-5-ene (DBN), 1,4-diazabicyclo[2.2.2]octane (DABCO) or sodium hydride, sodium ethoxide or the like. Alternatively the transformation can also be performed step-wise by addition of a secondary phosphine in the presence of a base such as e.g., potassium tert-butoxide or by addition of a preformed secondary lithium phosphide to yield the phosphine addition product and subsequent oxidation with hydrogen peroxide.

Step 7

The bisoxides (7) are reduced to the diphosphines (8) which optionally can be purified and stored as bis(borane) adducts (9) and which from the diphosphines can be regenerated by deboronation as depicted in scheme 3:

Scheme
(drawn for diastereoisomers (S, S)-8 and (S, R)-8; the diastereoisomers (R, R)-8 and (R, S)-8
can be prepared analogously from (S, R)-7 and (S, S)-7)

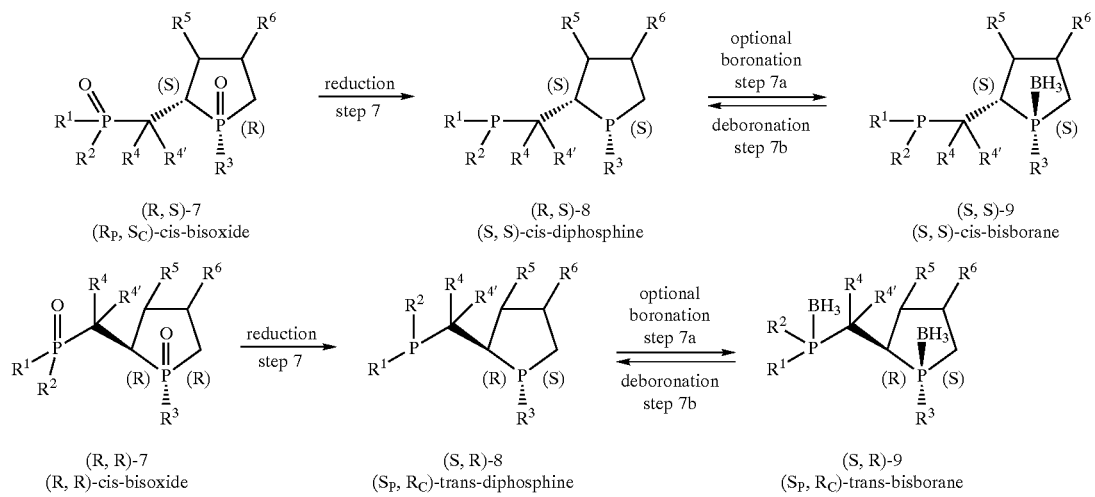

wherein the symbols are as defined above for formula I.

These methods are standards methods and known to the person skilled in the art. The reduction (step 7) can be achieved, for example, by treatment with silane reagents (e.g., trichlorosilane, hexachlorodisilane, phenylsilane, and polymethylhydrosiloxane), or with aluminum reagents (e.g., lithium or natrium aluminum hydride, and aluminum hydride). The boronation (step 7a) can be performed, for example, by treatment of the diphosphines with a borane-delivering agent such as e.g., the borane-tetrahydrofuran complex, the borane-N,N-diethylaniline complex, the borane-dimethylsulfide complex or the like. Alternatively, the reduction and boronation (steps 7 and 7a) can also be performed as a single protocol, e.g., by treatment of the bisoxides with lithium aluminum hydride in the presence of sodium borohydride and cerium trichloride, to provide directly the bis(borane) adducts. The bis(borane) adducts may be purified by chromatography or crystallization to achieve high chemical purity. The deboronation (step 7b) can be achieved by treatment of the bis(borane) adducts with an amine base such as e.g., 1,4-diazabicyclo[2.2.2]octane (DABCO), pyrrolidine, diethylamine or the like or by treatment with an acid such as $HBF_4$ or the like.

The optically active ligands of formula I form complexes with transition metals, especially with transition metals of Group VIII, such as ruthenium, rhodium, iridium, palladium and nickel. These complexes can be used as catalysts in asymmetric reactions such as hydrogenations and enantioselective hydrogen displacements in prochiral allylic systems. Preferably, the metal complexes are used in their isolated forms for the hydrogenations. Alternatively, the complexes may be prepared in situ.

These catalysts, i.e., the complexes of a transition metal and the chiral diphosphine ligands of formula I, are novel and are likewise an aspect of the present invention.

The aforementioned transition metal complexes, especially the complexes with metals of group VIII can be represented by the following formula II and III indicated below:

$$M_mL_nX_pA_q \quad\quad II$$

wherein
M is a transition metal,
L is the diphosphine compound of formula I;
X is a coordinating anion, such as Cl, Br or I
m, n and p are each 1, and
q is 0, if M is Rh;
or
X is acyloxy, such as acetoxy, trifluoroacetoxy or pivaloyloxy,
m and n are each 1,
p is 2, and
q is 0, if M is Ru;
or
X is Cl,
m and n are each 2,
p is 4,
q is 1, and
A is triethylamine, if M is Ru;
or
X is a π-methallyl group,
m and n are each 1,
p is 2, and
q is 0, if M is Ru;
or
X is a coordinating anion, such as Cl, Br or I,
m, n and p are each 1, and
q is 0, if M is Ir;
or
X is Cl,
m and n are each 1,
p is 2, and
q is 0, if M is Pd;
or
X is Cl, Br or I,
m and n are each 1,
p is 2, and
q is 0, if M is Ni.

$$[M_mL_nX_pA_q]D_r \quad\quad III$$

wherein
M is a transition metal,
L is the diphosphine compound of formula I,
X is a diene ligand, such as cod or nbd (both as defined below),
D is a non-coordinating anion, such as $BF_4$, $ClO_4$, $PF_6$, $SbF_6$, $CF_3SO_3$, $BPh_4$, or BARF (as defined below),
m, n, p and r are each 1, and
q is 0, if M is Rh;
or
X is an olefinic ligand, such as cyclooctene or ethylene,
D is a non-coordinating anion, such as $BF_4$, $ClO_4$, $PF_6$, $SbF_6$, $CF_3SO_3$, $BPh_4$, or BARF,
m, n and r are each 1,
p is 2 and
q is 0, if M is Rh;
or
X is Cl, Br or I,
A is benzene or p-cymene,
D is Cl, Br or I, and
m, n, p, q and r are each 1, if M is Ru;
or
D is a non-coordinating anion, such as $BF_4$, $ClO_4$, $PF_6$, $SbF_6$, $CF_3SO_3$, $BPh_4$, or BARF,
m and n are each 1,
p and q are each 0, and
r is 2, if M is Ru;
or
X is a diene ligand, such as cod or nbd,
D is a non-coordinating anion, such as e.g., $BF_4$, $ClO_4$, $PF_6$, $SbF_6$, $CF_3SO_3$, $BPh_4$, or BARF,
m, n, p and r are each 1, and
q is 0, if M is Ir;
or
X is an olefinic ligand, such as e.g., cyclooctene or ethylene,
D is a non-coordinating anion, such as e.g., $BF_4$, $ClO_4$, $PF_6$, $SbF_6$, $CF_3SO_3$, $BPh_4$, or BARF,
m, p and r are each 1,
n is 2, and
q is 0, if M is Ir;
or
X is a π-allyl group,
D is a non-coordinating anion, such as e.g., $BF_4$, $ClO_4$, $PF_6$, $SbF_6$, $CF_3SO_3$, $BPh_4$, or BARF,
m, n, p and r are each 1, and
q is 0, if M is Pd.

Ph is a phenyl group, cod is (Z,Z)-1,5-cyclooctadiene, nbd is norbornadiene, and BARF is tetrakis[3,5-bis(trifluoromethyl)phenyl]borate. π-Methallyl and π-allyl is anionic ligands of the structures $H_2C=C(Me)-CH_2$ and $H_2C=CH-CH_2$.

Preferred transition metal complexes and methods for making such complexes are described below.

A ruthenium complex can be prepared, for example, by reaction of the Ru precursors $[Ru(cod)(OCOCF_3)_2]_2$, [Ru (cod)(OCOCF$_3$)$_2$]$_2$.H$_2$O, [Ru(cod)(OCOCH$_3$)$_2$] or [Ru$_2$(cod)$_2$Cl$_4$(CH$_3$CN)] and the ligand of formula I in an inert solvent, for example, in ethers such as tetrahydrofuran or diethyl ether or mixtures thereof, or in dichloromethane as described in the literature (B. Heiser, E. A. Broger, Y. Crameri, Tetrahedron: Asymmetry 1991, 2, 51). Another method for preparing a ruthenium complex comprises, for example, the reaction of the ruthenium precursor [Ru(cod)(methallyl)$_2$] with a ligand of the formula I in a nonpolar solvent such as e.g., hexane or toluene or mixtures thereof as described in J. P. Genet, S. Mallart, C. Pinel, S. Juge, J. A. Laffitte, Tetrahedron: Asymmetry, 1991, 2, 43.

In situ preparation of ruthenium complexes can be performed, for example, by reaction of the ruthenium precursor [Ru(cod)(methallyl)$_2$] with a ligand of the formula I in the presence of trifluoroacetic acid in methanol as described in the literature (B. Heiser, E. A. Broger, Y. Crameri, Tetrahedron: Asymmetry 1991, 2, 51).

A ruthenium complex can also be prepared, for example, by heating [Ru(cod)Cl$_2$]$_n$ and the ligand of formula I at reflux by use of toluene as a solvent in the presence of triethylamine as described in the literature (T. Ikariya, Y. Ishii, H. Kawano, T. Arai, M. Saburi, and S. Akutagawa, J. Chem. Soc., Chem. Commun. 1985, 922). Further, a ruthenium complex can be prepared, for example, by heating [Ru(p-cymene)I$_2$]$_2$ and the ligand of formula I with stirring in a methylene chloride/ethanol mixture in accordance with the method described in the literature (K. Mashima, K. Kusano, T. Ohta, R. Noyori, H. Takaya, J. Chem. Soc., Chem. Commun. 1989, 1208).

Preferred ruthenium complexes are
Ru(OAc)$_2$(L), [Ru(OCOCF$_3$)$_2$(L)]$_2$, Ru$_2$Cl$_4$(L)$_2$.NEt$_3$, [RuCl(benzene)(L)]Cl, [RuBr(benzene)(L)]Br, [RuI(benzene)(L)]I, [RuCl(p-cymene)(L)]Cl, [RuBr(p-cymene)(L)]Br, [RuI(p-cymene)(L)]I, [Ru(L)](BF$_4$)$_2$, [Ru(L)](ClO$_4$)$_2$, [Ru(L)](PF$_6$)$_2$ and [Ru(L)](BPh$_4$)$_2$.

A rhodium complex can be prepared, for example, by reaction of rhodium precursors such as [Rh(cod)Cl]$_2$, [Rh(nbd)Cl]$_2$, [Rh(cod)$_2$]SbF$_6$, [Rh(cod)$_2$]BF$_4$, [Rh(cod)$_2$]ClO$_4$ with the ligand of formula I in accordance with the method described in "Experimental Chemistry, 4th edition" Vol.18, Organometallic Complexes, pp. 339–344, Ed. Chemical Society of Japan, 1991, Maruzen.

Preferred rhodium complexes are Rh(L)Cl, Ph(L)Br, Rh(L)I, [Rh(cod)(L)]SbP$_6$, [Rh(cod)(L)]BF$_4$, [Rh(cod)(L)]ClO$_4$, [Rh(cod)(L)]PF$_6$, [Rh(cod)(L)]BPh$_4$, [Rh(cod)(L)] BARF, [Rh(nbd)(L)]SbF$_6$, [Rh(nbd)(L)]BF$_4$, [Rh(nbd)(L)] ClO$_4$, and [Rh(nbd)(L)]PF$_6$, [Rh(nbd)(L)]BPh$_4$.

An iridium complex can be prepared, for example, by reacting the ligand of formula I with [Ir(cod)(CH$_3$CN)$_2$]BF$_4$ or with [Ir(cod)Cl]$_2$ in accordance with the method described in the literature (K. Mashima, T. Akutagawa, X. Zhang, H. Takaya, T. Taketomi, H. Kumobayashi, S. Akutagawa, J. Organomet., Chem. 1992, 428, 213).

Preferred iridium complexes are Ir(L)Cl, Ir(L)Br, Ir(L)I, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]BF$_4$, [Ir(nbd)(L)]ClO$_4$, [Ir(nbd)(L)] PF$_6$, and [Ir(nbd)(L)]BPh$_4$ A palladium complex can be prepared, for example, by reaction of the ligand of formula I with π-allylpalladium chloride in accordance with the method described in a literature (Y. Uozumi and T. Hayashi, J. Am., Chem. Soc. 1991, 113, 9887).

Preferred palladium complexes are PdCl$_2$(L), [Pd(π-allyl)(L)]BF$_4$, [(Pd(π-allyl)(L)]ClO$_4$, [(Pd(π-allyl)(L)]PF$_6$, and [(Pd(π-ally)(L)]BPh$_4$ A nickel complex can be prepared, for example, by dissolving the ligand of formula I and nickel chloride in an alcohol such as isopropanol or ethanol or mixtures thereof and heating the solution with stirring in accordance with the method described in "Experimental Chemistry, 4th edition" Vol.18, Organometallic Complexes, pp. 376, Ed. Chemical Society of Japan, 1991, Maruzen.

Preferred examples of nickel complexes are NiCl$_2$(L), NiBr$_2$(L) and NiI$_2$(L).

The transition metal complexes prepared as described above can be used as catalysts for asymmetric reactions, in particular for asymmetric hydrogenation reactions.

The following examples serve to illustrate the invention and do not in any manner represent a limitation.

In the examples the selected abbreviations have the follow meanings:
h hour
m.p. melting point
THF tetrahydrofuran
EtOAc ethyl acetate
DBU 1,8-diazabicyclo(5,4,0)undec-7-ene
DABCO 1,4-diazabicyclo[2.2.2]octane
BARF tetrakis[3,5-bis(trifluoromethyl)phenyl]borate
c concentration
S/C molar substrate catalyst ratio
conv. conversion
ee enantiomeric excess
GC gaschromatography
PMP5 2-[(diphenylphosphino)methyl]-1-phenyl-phospholane
cod (Z,Z)-1,5-cyclooctadiene All experiments were carried out under an atmosphere of deoxygenated argon. Solvents were dried and distilled under argon before use. The metal diphosphine complexes were prepared using Schlenk techniques.

EXAMPLE 1

Preparation of 1-Phenyl-2-phospholanemethanol-1-oxide

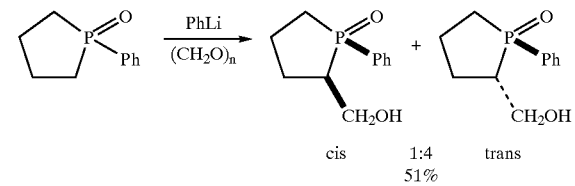

cis 1:4 trans
51%

In a 1 l round bottom 2-neck flask charged a with a magnetic stirring bar, 23.4 g 1-phenylphospholane-1-oxide (0.11 mol) was dissolved in 300 ml freshly distilled THF, and 10.4 g dry paraformaldehyde was added. The reaction flask was flushed with argon and cooled to −20° C. Subsequently 100 ml phenyllithium solution in cyclohexane/diethylether 7:3 (1.8M) was added in one portion. The resulting mixture was stirred until the temperature reached +10° C. and additionally 5 minutes at that temperature. Then 10 g NH$_4$Cl was added. The mixture was filtered, concentrated, and the residue purified by flash chromatography (EtOAc, followed by EtOAc/methanol 10:1). Yields: 2.5 g substrate (1-phenylphospholane-1-oxide) (11%), 11.7 g (43%) trans-1-phenyl-2-phospholanemethanol-1-oxide as white crystals, m.p. 109–110° C. (toluene); $^1$H NMR (500 MHz) δ: 1.70–1.85 (m, 1H), 1.95–2.30 (m, 6H), 3.90–4.00 (m, 2H), 4.19 (t, 1H, J=6.1), 7.45–7.55 (m, 3H), 7.70–7.76 (m, 2H); $^{31}$P NMR (200 MHz) δ: 63.3; and 2.2 g (8%) cis-1-phenyl-2-phospholanemethanol-1-oxide, white crystals, m.p. 149–151° C. (toluene); $^1$H NMR (500 MHz)

δ: 1.46–1.57 (m, 1H), 2.02–2.22 (m, 4H), 2.28–2.42 (m, 1H), 2.44–2.58 (m, 1H), 3.32–3.49 (m, 2H), 3.76 (t, 1H, J=5.7), 7.46–7.51 (m, 2H.), 7.52–7.57 (m, 1H), 7.67–7.73 (m, 2H); $^{31}$P NMR (200 MHz) δ: 62.7.

EXAMPLE 2

Preparation of 1-Phenyl-2-methylenephospholane-1-oxide

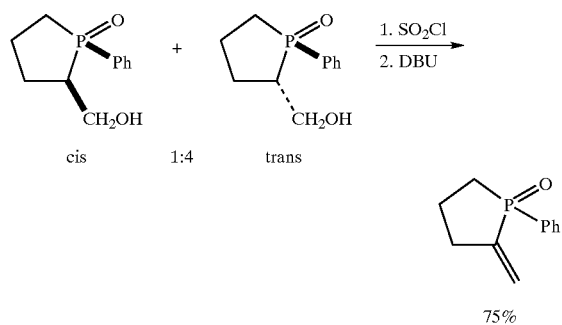

In a 100 ml round bottom 2-neck flask charged with a magnetic stirring bar and 20 ml freshly distilled CH$_2$Cl$_2$, 1.6 g 1-phenyl-2-phospholanemethanol-1-oxide (0.008 mol, mixture of diastereoisomers) was dissolved. The reaction flask was flushed with argon and cooled to 0° C. Subsequently 2.1 ml SOCl$_2$ in 10 ml CH$_2$Cl$_2$ was added dropwise. The resulting yellowish mixture was stirred for 5 h at room temperature, then 20 ml water was added. The mixture was extracted twice with 20 ml CH$_2$Cl$_2$, and the combined organic phases were dried over MgSO$_4$ and filtered. To the resulting filtrate containing crude 2-chloromethyl-1-phenylphospholane 1-oxide (mixture of isomers; $^{31}$P NMR (200 MHz) δ: 58.2, 60.3) 1.7 ml DBU was added. The mixture was heated and refluxed overnight. Evaporation of the solvent and flash chromatography of the residue with EtOAc/ethanol 20:1 yielded 1.1 g (75%) 1-phenyl-2-methylenephospholane-1-oxide as a colorless oil. $^1$H NMR (500 MHz) δ: 1.72–1.89 (m, 1H), 1.94–2.16 (m, 3H), 2.48–2.59 (m, 1H), 2.66–2.78 (m, 1H), 5.74 (dt, 1H, J=2.4, J=17.2), 5.88 (dt, 1H, J=2.1, J=36.6), 7.37–7.48 (m, 3H), 7.63–7.70 (m, 2H); $^-$P NMR (200 MHz) δ: 45.0.

EXAMPLE 3

Preparation of 1-Phenyl-2-methylenephospholane

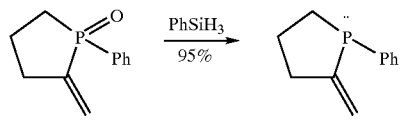

In a 250 ml round bottom 2-neck flask charged with a magnetic stirring bar and 60 ml freshly distilled toluene, 8.5 g 1-phenyl-2-methylenephospholane-1-oxide (0.04 mol) was dissolved and 11 g of PhSiH$_3$ was added. The flask was flushed with argon and the reaction mixture heated to 60° C. for 2 days. Then the solvent was evaporated and the residue purified by flash chromatography (hexane followed by hexane/EtOAc 15:1) to yield 7.4 g (95%) of 1-phenyl-2-methylenephospholane as a colorless oil, $^1$H NMR (200 MHz) δ: 1.55–2.10 (m, 4H), 2.20–2.65 (m, 2H), 5.51 (dd, 1H, J=1.6, J=11.0), 5.76 (dd, 1H, J=1.5, J=28.7), 7.05–7.50 (m, 5H), $^{31}$P NMR (200 MHz) δ: –12.6.

EXAMPLE 4a

Preparation of (1R)- and (1S)-1-Phenyl-1-[2-[(L)-methyloxy]-2-oxoethyl]-2-methylene-phospholanium hexafluorophoslphate Alternative name {(1R)- and (1S)-1-Carboxymethyl-1-phenyl-2-methylenephospholanium hexafluorophosphate (L)-methyl ester}

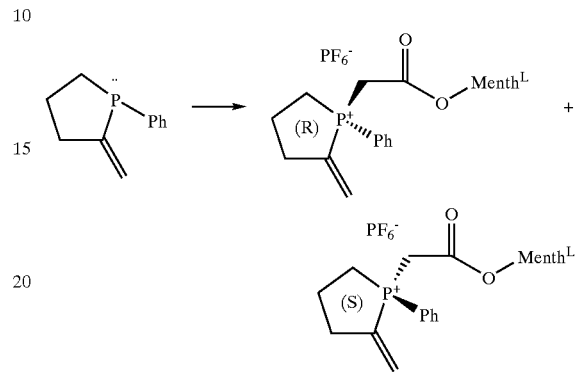

In a 250 ml round bottom 1-neck flask charged with a magnetic stirring bar and 50 ml EtOAc, 7.4 g 1-phenyl-2-methylenephospholane (0.04 mol) was dissolved and 12.8 g (L)-methyl bromoacetate was added. The mixture was stirred for 1.5 h; subsequently the solvent was evaporated. The oily residue was dissolved in 80 ml methanol and the solution was added dropwise to 7.5 g NH$_4$ PF$_6$ dissolved in 40 ml water. The mixture turned turbid, and the formation of white oil was observed on the bottom. After standing overnight, white precipitate had formed. The precipitate was filtered and washed with water and 20 ml ethanol to afford 18.45 g of 1-phenyl-1-[2-[(L)-methyloxy]-2-oxoethyl]-2-methylenephospholanium hexafluorophosphate (1:1 mixture of diastereoisomers) as a white solid. This material was dissolved by heating it in 100 ml ethanol. The white crystals formed after standing overnight were collected. The procedure was repeated 5 times, until $^1$H NMR showed diastereomeric purity.

Yield 5.02 g (24%) of diastereomerically pure (1R)-1-phenyl-1-[2-[(L)-methyloxy]-2-oxoethyl]-2-methylenephospholanium hexafluorophosphate as white crystals; m.p. 148.8–149.7° C. (ethanol); [α]$_D$=+47.2 (c=1.09, CHCl$_3$); $^1$H NMR (500 MHz) δ: 0.56 (d, J=6.9, 3H), 0.81 (d, J=7.0, 3H), 0.88 (d, J=6.5, 3H), 0.91–1.1 (m, 2H), 1.29–1.45 (m, 2H), 1.51–1.60 (m, 2H), 1.60–1.68 (m, 2H), 1.81–1.88(m, 1H), 1.98–2.12 (m, 1H), 2.33–2.48 (m, 1H), 2.72–2.82 (m, 1H), 2.83–3.12 (m, 3H), 4.02 (dd, J=1.3, J=13.7, 2H), 4.64 (dt, J=4.4, J=11.0, 1H), 6.46 (d, J=18.9, 1H), 6.55 (d, J=42.9, 1H), 7.63–7.69 (m, 2H), 7.72–7.78 (m, 1H), 7.80–7.87 (m, 2H); $^{31}$P NMR (500 MHz) δ 31.3.

From the mother liquors fractional crystallization from methanol provided diastereomerically pure (1S)-1-phenyl-1-[2-[(L)-methyloxy]-2-oxoethyl]-2-methylenephospholanium hexafluorophosphate; m.p. 131.5–133° C. (methanol); [α]$_D$=–116 (c=1.03, CHCl$_3$); $^1$H NMR (500 MHz) δ: 0.64 (d, J=6.9, 3H), 0.82 (d, J=7.0, 3H), 0.85 (d, J=6.5, 3H), 0.87–1.2 (m, 2H), 1.29–1.43 (m, 2H), 1.60–1.70 (m, 2H), 1.70–1.77 (m, 1H), 2.01–2.14 (m, 1H), 2.32–2.46 (m, 1H), 2.75–3.08 (m, 4H), 3.99 (dq, J=13.7, J=31.3, 2H), 4.66 (dt, J=4.4, J=11.0, 1H), 6.42 (d, J=18.8, 1H), 6.54 (d, J=42.8, 1H), 7.63–7.69 (m, 2H), 7.72–7.78 (m, 1H), 7.80–7.88 (m, 2H); $^{31}$P NMR (500 MHz) δ 31.2.

EXAMPLE 4b

Preparation of (1S)-1-Phenyl-1-[2-[(D)-methyloxy]-2-oxoethyl]-2-methylenephospholanium hexafluorophosphate In analogy to Example 4a, reaction of 1-phenyl-2-methylenephospholane with (D)-methyl bromoacetate provided diastereomerically pure (1S)-1-phenyl-1-[2-[(D)-methyloxy]-2-oxoethyl]-2-methylenephospholanium hexafluorophosphate; $[\alpha]_D = -44.3$ (c=1.15, CHCl$_3$); NMR as above for (1R)-1-phenyl-1-[2-[(L)-methyloxy]-2-oxoethyl]-2-methylenephospholanium hexafluorophosphate (Example 4a).

EXAMPLE 5a

Preparation of (R)-1-Phenyl-2-methylenephospholane-1-oxide

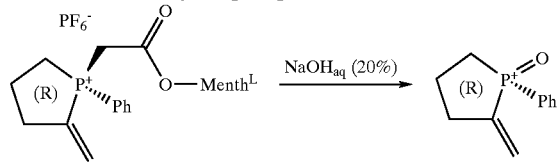

In a 250 ml round bottom 1-neck flask charged with a magnetic stirring bar and 50 ml CH$_2$Cl$_2$, 9.16 g of (1R)-1-phenyl-1-[2-[(L)-methyloxy]-2-oxoethyl]-2-methylenephospholanium hexafluorophosphate was dissolved and 50 ml NaOH (20% aqueous solution) was added. The mixture was vigorously stirred for 2 h, then 100 ml water was added and the mixture extracted 3 times with 30 ml CH$_2$Cl$_2$. The combined organic phases were dried over MgSO$_4$, filtered and evaporated. The residue was purified by flash chromatography with EtOAc/ethanol 20:1 to yield 3.2 g (95%) of (R)-1-phenyl-2-methylenephospholane-1-oxide as a colorless oil; $[\alpha]_D = +107.9$ (c=2.21, CHCl$_3$), NMR as above (Example 2).

EXAMPLE 5b

Preparation of (S)-1-Phenyl-2-methylenephospholane-1-oxide

Analogously, treatment of (1S)-1-phenyl-1-[2-[(D)-methyloxy]-2-oxoethyl]-2-methylenephospholanium hexafluorophosphate (or of (1S)-1-phenyl-1-[2-[(L)-methyloxy]-2-oxoethyl]-2-methylenephospholanium hexafluorophosphate) with NaOH (20%) provided (S)-1-phenyl-2-methylenephospholane-1-oxide as a colorless oil; NMR as above (Example 2).

EXAMPLE 6

Preparation of (1R,2S)-cis-1-Phenyl-2-[(diphenylphosphinoyl)methyl]phospholane-1-oxide {(1R,2S)-cis-bis-oxide}

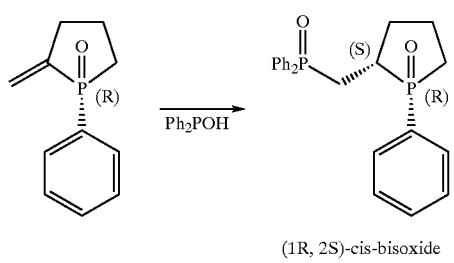

(1R, 2S)-cis-bisoxide

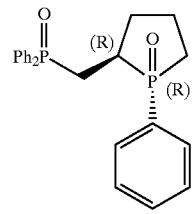

(R, R)-trans-bisoxide (1R,2S)-cis-bisoxide (R,R)-trans-bisoxide

A 250 ml round bottom 2-neck flask equipped with a magnetic stirring bar was charged with a solution of 3.8 g of (R)-1-phenyl-2-methylenephospholane-1-oxide in 100 ml toluene. Then 4.35 g diphenylphosphine oxide was added to this solution. The mixture was heated under reflux overnight. The solvent was evaporated and the residue purified by flash chromatography with EtOAc/methanol 10:1 to yield 2.35 g (30%) of (1R,2R)-trans-1-phenyl-2-[(diphenylphosphinoyl)methyl]-phospholane-1-oxide {R,R-trans-bisoxide} as a colorless oil $^1$H NMR (500 MHz) δ: 1.60–1.74 (m, 2H), 1.93–2.06 (m, 1H), 2.09–2.46 (m, 4H), 2.49–2.57 (m, 1H), 2.75–2.86 (m, 1H), 7.28–7.34 (m, 2H), 7.38–7.53 (m, 7H), 7.56–7.66(m, 4H), 7.73–7.80 (m, 2H); $^{31}$P NMR (200 MHz) δ: 31.8 (d, J=42.4), 59.1 (d, J=42.4); $[\alpha]_D = +77.1$ (c=1.16, CHCl$_3$); and 2.92 g (37%) of (1R,2S)-cis-1-phenyl-2-[(diphenylphosphinoyl)methyl]-phospholane-1-oxide {1R,2S-cis-bisoxide}, as white crystals, mp.176° C. (toluene); $^1$H NMR (500 MHz) δ: 1.50–1.75 (m, 2H), 1.93–2.25 (m, 4H), 2.30–2.50 (m, 2H), 2.53–2.70 (m, 1H), 7.35–7.80 (m, 15H.), $^{31}$P NMR (200 MHz) δ: 33.1 (d, J=51.5), 65.5 (d, J=51.5). $[\alpha]_D = +98.6$ (c=1.01, CHCl$_3$).

EXAMPLE 7

Preparation of (1S,2S)-cis-[1-Phenyl-2-[(diphenylphosphino)methyl]phospholane]bisborane Alternative name {Hexahydro[μ-[(1S,2S)-[1-phenyl-2-[(diphenylphosphino-κP) methyl]-phospholane-κP]diboron}

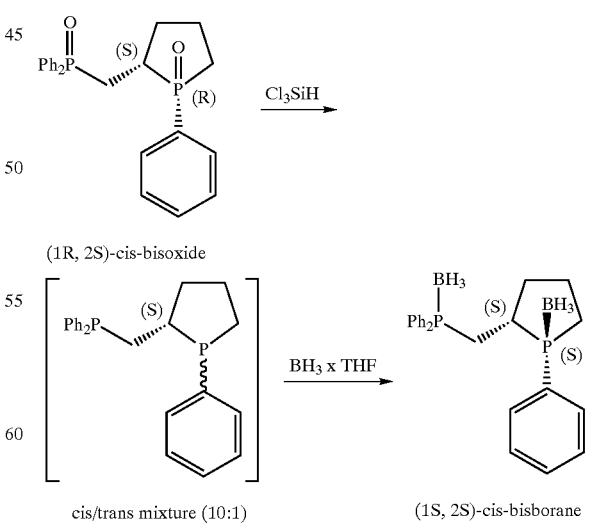

A 250 ml round bottom 2-neck flask equipped with a magnetic stirring bar was flushed with argon and charged with 20 ml triethylamine and 80 ml dry toluene. Then 9 ml Cl$_3$SiH was added by syringe through a septum and 2.35 g of (1R,2S)-cis-1-phenyl-2-[(diphenylphosphinoyl)methyl]phospholane-1-oxide dissolved in 50 ml dry toluene was added dropwise. The mixture was heated under reflux for 3.5 h. Subsequently 100 ml 20% aqueous NaOH was added and the mixture left overnight with stirring. The organic phase was separated and the water phase extracted twice with 80 ml toluene. The organic phases were collected, dried over Na$_2$SO$_4$, filtered and evaporated. The residue was purified by flash chromatography on Al$_2$O$_3$ with hexane followed by hexane/EtOAc 20:1. To the collected fractions containing the diphosphine 15 ml of a solution of BH$_3$ in THF (1M) was added. After 1 h the solvent was evaporated and the residue purified by flash chromatography with hexane/EtOAc 5:1 to yield 1.82 g (78%) of (1S,2S)-cis-[1-phenyl-2-[(diphenylphosphino)methyl]-phospholane]bisborane as white crystals, mp. 118–119° C. (hexane:ethyl acetate); $^1$H NMR (500 MHz) δ: 0.35–1.35 (bt, 6H, 2xBH$_3$), 1.35–1.50 (m, 1H), 1.50–1.63 (m, 1H), 1.70–1.85 (m, 1H), 2.15–2.55 (m, 6H) 7.3–7.8 (m, 15H, ar.).

EXAMPLE 8a

Preparation of (1S,2S)-cis-1-Phenyl-2-[(diphenylphosphino)methyl]phospholane {(S,S)-cis-PMP5}

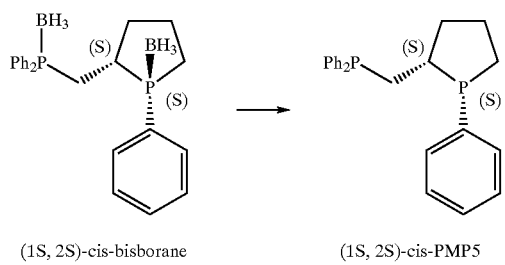

(1S, 2S)-cis-bisborane     (1S, 2S)-cis-PMP5

In a 100 ml round bottom 2-neck flask flushed with argon and equipped with a magnetic stirring bar, 155 mg DABCO was dissolved in 30 ml dry toluene. 270 mg of (1S,2S)-cis-[1-phenyl-2-[(diphenylphosphino)methyl]phospholane]bisborane was added and the mixture was stirred at 40° C. overnight. The solvent was evaporated and the residue purified by flash chromatography on Al$_2$O$_3$ (hexane/EtOAc 20:1) to afford 240 mg (96%) of (1S,2S)-cis-1-phenyl-2-[(diphenylphosphino)methyl]phospholane {(S,S)-cis-PMP5} as a turbid oil which solidified after standing for a few days yielding white powder, m.p. 74.5° C.; $^{31}$P NMR (200 MHz) δ: -16.3 (d, J=26.6), -6.7 (d, J=26.6); Elemental Anal. Calcd. for C$_{23}$H$_{24}$P$_2$: C, 76.26%; H, 6.68%; P, 17.09%; found C, 78.18%; H, 6.62%; P, 17.20%.

EXAMPLE 8b

Preparation of (1R,2R)-cis-1-Phenyl-2-[(diphenylphosphino)methyl]phospholane {(R,R)-cis-PMP5}

This ligand was prepared from (S)-1-phenyl-2-methylenephospholane-1-oxide analogously as described for (S,S)-cis-PMP5 in Examples 6–8a. (1R,2R)-cis-1-phenyl-2-[(diphenylphosphino)methyl]phospholane {(R,R)-cis-PMP5} turbid oil which solidified after standing for a few days; white powder, m.p. 74° C.; [α]$_D$=-159.1 (c=1.18, C$_6$H$_6$); $^{31}$P NMR as above.

EXAMPLE 9

In the alternative approach the 1-phenyl-2-methylenephospholane-1-oxide (from example 2) can be separated into the enantiomerically pure 1-phenyl-2-methylenephospholane-1-oxide by chromatography on a chiral support.

Resolution of 1-phenyl-2-methylenephospholane-1-oxide by preparative chromatography on a chiral support Phenyl-2-methylenephospholane-1-oxide (3.0 g, chemical purity ca. 80%) was separated by repeated injections on a CHIRALPAK® AD 20 µm column (250×50 mm; mobile phase 100% acetonitrile, flow rate 120 ml/min) to afford 0.9 g of (S)-1-phenyl-2-methylenephospholane-1-oxide (ee 100%, chemical purity 95%; [α]$_D$=-99.6 (c=1.03, CHCl$_3$) and 1.0 g of (R)-1-phenyl-2-methylenephospholane-1-oxide (ee 99.4%, chemical purity 99.5%; [α]$_D$=+106.8 (c=1.00, CCHCl$_3$).

EXAMPLE 10

Preparation of 2-(Dicyclohexyl-phosphinoylmethyl)-1-phenyl-phospholane 1-oxide

Step 1

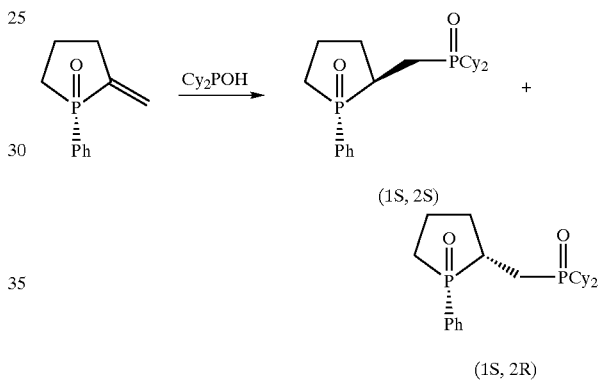

wherein Cy signifies cyclohexyl.

In a 250 ml round bottom 2-neck flask charged with a magnetic stirring bar 5.0 g (26 mmol) (S)-2-methylene-1-phenyl-phospholane 1-oxide and 5.6 g dicyclohexylphosphine oxide was dissolved in 100 ml dry THE 1.2 g (2 eq.) of potassium tert-butoxide was added and the reaction was stirred overnight. Next 500 ml of water was added and the mixture was extracted with chloroform (4×100 mL). Organic phase was dried over MgSO$_4$, concentrated and purified by chromatography (ethyl acetate: methanol 10:1). Yield: 4.99 g (47%) of (1S,2S)-2-[(dicyclohexylphosphinoyl)methyl]-1-phenyl-phospholane 1-oxide as white crystals, mp 110–114° C. (ethyl acetate); $^1$H NMR (500 MHz) δ 0.94–1.14 (m, 5H), 1.16–1.36 (m, 5H), 1.43–1.63 (m, 5H), 1.65–1.88 (m, 8H), 1.88–1.97 (m, 2H), 1.99–2.13 (m, 2H), 2.15–2.35 (m, 3H), 2.47–2.69 (m, 1H), 7.42–7.57 (m 3H), 7.63–7.74 (m, 2H); $^{13}$C NMR (126 MHz) δ: 20.2 (d, J=58.7), 23.4 (d, J=5.9), 25.2–26.8 (m), 29.4 (d, J=66.9), 33.9 (d, J=9.5), 34.6 (dd, J=4.3, J=67.2), 36.8 (d, J=64.1), 37.0 (d, J=64.2), 128.7 (d, J=11.5), 103.1 (d, J=9.6), 131.9 (d, J=2.8), 133.4 (d, J=88.3); -$^{31}$P NMR (162 MHz) δ: 51.7 (d, J=34.8), 59.3 (d, J=34.8); EI MS m/z (%): 406 (2, M$^+$), 324 (12), 323 (35), 242 (23), 241 (100), 193 (43), 179 (14), 146 (14), 55 (10); HR MS calcd. for C$_{23}$H$_{36}$O$_2$P$_2$: 406.2191, found 406.2185; [α]$_D$-43.5°

(c=1.48, CHCl$_3$); and 4.64 g (44%) of (1S,2R)-2-[(dicyclohexylphosphinoyl)methyl]-1-phenyl-phospholane 1-oxide as a white solid, mp 90–130° C. (ethyl acetate); $^1$H NMR (500 MHz) δ: 0.95–1.36 (m, 10H), 1.40–1.65 (m, 5H), 1.65–1.89 (m, 9H), 2.02–2.23 (m, 4H), 2.37–2.53 (m, 2H), 2.64–2.79 (m, 1H), 7.47–7.57 (m, 3H), 7.65–7.72 (m, 2H); $^{13}$C NMR (126 MHz) δ: 22.0 (d, J=57.6), 22.3 (d, J=5.6), 25.1–26.6 (m), 32.0 (d, J=12.6), 36.3 (d, J=65.5), 36.8 (d, J=64.1), 37.2 (dd, J=5.0, J=65.6), 128.7 (d, J=11.1), 130.9 (d, J=8.8), 131.3 (d, J=87.7), 132.0 (d, J=2.7); $^{31}$P NMR (162 MHz) δ: 51.0 (d, J=41.4), 64.3 (d, J=41.4); EI MS m/z (%): 406 (1, M$^+$), 241 (100), 193 (57), 179 (19), 146 (22), 55 (18), 41 (16); HR MS calcd. for C$_{23}$H$_{36}$O$_2$P$_2$: 406.2191, found 406.2182; [α]$_D$=−36.4° (c=1.67, CHCl$_3$).

Step 2

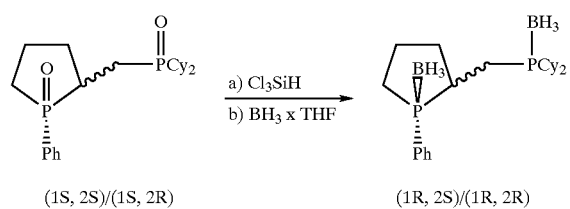

(1S, 2S)/(1S, 2R)      (1R, 2S)/(1R, 2R)

The same procedure as for transformation of diphenylphosphinoyl derivatives described in Example 2 was employed. Yield: 81% of (1R,2S)-2-[(dicyclohexylphosphanyl)methyl]-1-phenyl-phospholane P,P-diborane as white crystals, mp 138.5° C. (ethyl acetate); $^1$H NMR (500 MHz) δ: −0.1–0.9 (b, 6H), 0.9–1.1 (m, 6H), 1.1–1.4 (m, 6H), 1.45–2.0 (m, 13H), 2.05–2.3 (m, 4H), 2.5–2.7 (m, 2H), 7.42–7.52 (m, 3H), 7.68–7.77 (m, 2H); $^{13}$C NMR (126 MHz) δ: 18.0 (dd, J=6.8, J=29.9), 25.7–26.8 (m), 32.0 (d, J=32.5), 32.5 (d, J=31.9), 36.0 (d, J=34.6), 36.0 (d, J=7.35), 128.9 (d, J=9.7), 130.3 (d, J=45.6), 131.5 (d, J=2.6), 131.7 (d, J=8.9); $^{31}$P NMR (202 MHz) δ: 28.5 (b), 38.3 (b); LSIMS(+) MS m/z: 425 (5, M+Na)$^+$, 402 (25), 275 (75); Elemental Anal. Calcd. for C$_{23}$H$_{42}$B$_2$P$_2$: C, 68.69; H, 10.53; found C, 68.53; H, 10.69; [α]$_D$=−76.2° (c=0.80, CHCl$_3$).

Using the same procedure but with the (1S,2R) derivative as a substrate yielded 84% of (1R,2R)-2-[(dicyclohexylphosphanyl)methyl]-1-phenyl-phospholane P,P-diborane as white crystals, mp 113.5–115° C. (ethyl acetate); $^1$H NMR (500 MHz) δ: −0.1–0.8 (b, 4H), 0.8–1.15 (m, 5H), 1.17–1.34 (m, 6H), 1.35–1.63 (m, 4H), 1.65–2.01 (m, 12H), 2.03–2.35 (m, 4H), 2.41–2.61 (m, 2H), 7.43–7.53 (m, 3H), 7.63–7.76 (m, 2H); $^{13}$C NMR (126 MHz) δ: 15.7 (d, J=1.7), 23.5 (dd, J=8.5, J=36.6), 25.9–28.4 (m), 31.5 (d, J=28.8), 32.3 (d, J=29.7), 35.5 (d, J=33.1), 39.6 (dd, J=1.4, J=24.1), 126.4 (d, J=44.4), 128.8 (d, J=9.6), 131.8 (d, J=2.4), 133.0 (d, J=8.8); $^{31}$P NMR (202 MHz) δ: 30.8 (b), 40.4 (b); LSIMS(+) MS m/z: 425 (14, (M+Na)$^+$) 401 (100), 387 (66), 375 (47); Elemental Anal. Calcd. for C$_{23}$H$_{42}$B$_2$P$_2$: C, 68.69; H, 10.53; found C, 68.47; H, 10.36; [α]$_D$=−15.60 (c=0.77, CHCl$_3$).

EXAMPLE 11

Preparation of 2-[Bis-(3,5-di-tert-butyl-phenyl)-phosphinoylmethyl]-1-phenyl-pholane 1-oxide Step 1

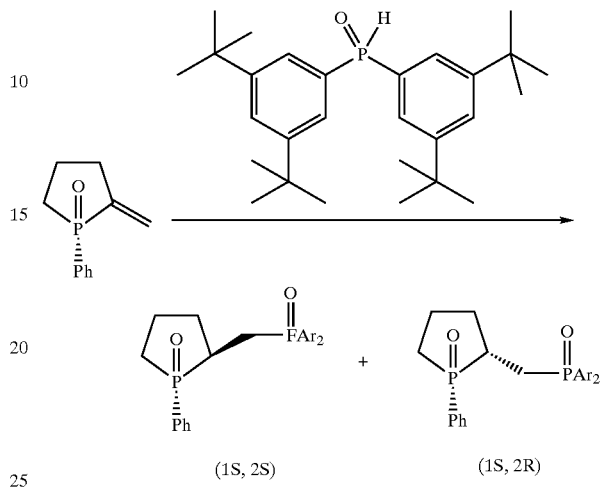

(1S, 2S)      (1S, 2R)

wherein Ar is di-tert-butyl-phenyl

The same procedure as for synthesis of diphenylphosphinoyl derivatives described in Example 6 was employed. Yield: 11% of (1S,2S)-2-[di(3,5-(di-tert-butyl-phenyl))phosphinoyl)methyl]-1-phenyl-phospholane 1-oxide as white powder; mp 149–150° C. (hexane); $^1$H NMR (500 MHz) δ: 1.22 (s, 18H), 1.30 (s, 18H), 1.56–1.82 (m, 2H), 1.91–2.06 (m, 1H), 2.08–2.23 (m, 2H), 2.24–2.54 (m, 3H), 2.63–2.73 (m, 1H), 7.36–7.43 (m, 2H), 7.44–7.52 (m, 4H), 7.53–7.62 (m, 5H); $^{13}$C NMR (126 MHz) δ: 23.5 (d, J=6.4), 28.2 (dd, J=2.3, J=69.5), 29.4 (d, J=66.8), 31.2 (i), 31.3 (i), 32.3 (dd, J=1.5, J=9.6), 34.2 (dd, J=3.9, J=66.7), 34.9, 35.0, 124.7 (d, J=3.4), 124.8 (d, J=3.7), 125.8 (d, J=2.6), 125.9 (d, J=2.7), 128.7 (d, J=11.5), 129.9 (d, J=9.6), 131.6 (d, J=98.3), 131.7 (d, J=2.8), 132.8 (d, J=97.0), 133.1 (d, J=88.5), 151.1 (d, J=11.5); $^{31}$P NMR (202 MHz) δ: 34.9 (d, J=43.8), 60.4 (d, J=43.8); EI MS m/z (%): 619 (19), 618 (47, M$^+$), 617 (12), 603 (10), 590 (26), 589 (56), 577 (37), 576 (100), 575 (56), 549 (11), 541 (20), 472 (10), 441 (22), 440 (31), 430 (27), 429 (99), 426 (14), 425 (24), 409 (13), 193 (37), 57 (36), 41 (10); Elemental Anal. Calcd. for C$_{39}$H$_{56}$O$_2$P$_2$: C, 75.70; H, 9.12; found C, 75.32; H, 9.47; [α]$_D$=−56.3° (c=0.95, CHCl$_3$); and 83% of (1S,2R)-2-[di(3,5-(di-tert-butyl-phenyl))phosphinoyl)methyl]-1-phenyl-phospholane 1-oxide as white powder, mp 198–199° C. (hexane/ethyl acetate); $^1$H NMR (500 MHz) δ: 1.26 (s, 18H), 1.30 (s, 18H), 1.47–1.69 (m, 2H), 1.92–2.21 (m, 5H), 2.29–2.60 (m, 2H), 7.41 (dd, J=1.8, J=12.0, 2H), 7.46 (dd, J=1.8, J=12.2, 2H), 7.49–7.59 (m, 5H), 7.69–7.75 (m, 2H); $^{13}$C NMR (126 MHz) δ: 22.5 (d, J=5.8), 25.8 (d, J=66.7), 29.5 (d, J=69.0), 31.1 (d, J=12.3), 31.2 (i), 31.3 (i), 35.0, 34.98, 35.01, 37.0 (dd, J=4.5, J=65.6), 124.8 (d, J=9.7), 125.0 (d, J=10.0), 125.8 (d, J=2.6), 126.1 (d, J=2.6), 128.7 (d, J=11.2), 130.9 (d, J=98.2), 130.9 (d, J=8.8), 131.4 (d, J=86.8), 132.0 (d, J=2.8), 132.2 (d, J=99.4), 151.1 (d, J=11.3), 151.2 (d, J=11.4); $^{31}$P NMR (202 MHz) δ: 34.9 (d, J=50.8), 65.2 (d, J=50.8); EI MS m/z (%): 619 (28), 618 (69, M$^+$), 603 (13), 591 (10), 590 (38), 589 (79), 577 (36), 576 (100), 575 (52), 549 (13), 472 (16), 442 (18), 441 (70), 440 (100), 439 (18), 426 (25), 425 (47), 409 (19), 398 (17), 384 (16), 294 (12), 193 (56), 57 (42), 41 (11); HR MS calcd. for $C_{39}H_{56}O_2P_2$: 618.3756, found 618.3736; $[\alpha]_D$=−46.6° (c=0.99, CHCl$_3$).

Step 2

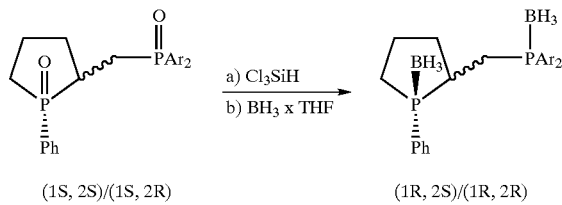

(1S, 2S)/(1S, 2R)     (1R, 2S)/(1R, 2R)

The same procedure as for transformation of diphenylphosphinoyl derivatives was employed as described in Example 7. Yield 81% of (1R,2S)-2-[di(3,5-(di-tert-butyl-phenyl))-phosphanyl)methyl]-1-phenyl-phospholane P,P-diborane; $^{31}$P NMR (202 MHz) δ: 17.4 (b), 39.9 (b).

Using the same procedure but the (1S,2R) derivative as a substrate yielded 79% of (1R,2R)-2-[di(3,5-(di-tert-butyl-phenyl))phosphanyl)methyl]-1-phenyl-phospholane PP-diborane; $^1$H NMR (500 MHz) δ: 0.25–0.92 (b, 6H), 1.16 (s, 18H), 1.23 (s, 18H), 1.27–1.42 (m, 2H), 1.43–1.53 (m, 1H), 1.60–1.74 (m, 1H), 2.03–2.37 (m, 5H), 7.25 (dd, J=1.7, J=11.2, 2H), 7.36–7.49 (m, 7H), 7.58–7.67 (m, 2H); $^{13}$C NMR (126 MHz) δ: 23.6 (d, J=36.0), 25.2, 26.8 (d, J=34.2), 31.2 (i), 31.3 (i), 33.5, 35.0, 35.1, 35.9 (d, J=32.9), 125.1 (d, J=2.3), 125.7 (d, J=2.3), 125.9 (d, J=9.7), 126.4 (d, J=9.8), 126.9 (d, J=54.2), 127.6 (d, J=42.6), 128.8 (d, J=9.2), 129.3 (d, J=54.6), 131.7 (d, J=2.4), 132.9 (d, J=8.4), 151.1 (d, J=9.6), 151.4 (d, J=9.7); $^{31}$P NMR (202 MHz) δ: 17.6 (b), 40.2 (b); LSIMS(+) MS m/z: 637 (17, M+Na)$^+$, 614 (43, M$^+$), 611 (100), 599 (84), 587 (60).

EXAMPLE 12

Synthesis of 2-(1-diphenylphosphinoyl-1-methyl-ethyl)-1-phenylphospholane 1-oxide Step 1

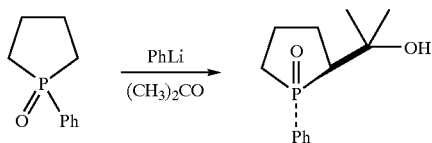

A 500 mL round bottom 2-neck flask equipped with a magnetic stirring bar was charged with 7.2 g of 1-phenylphospholane-1-oxide (40 mmol) dissolved in 200 mL of THF and cooled to −78° C. (dry ice/acetone bath). Subsequently 40 mL (1.3 eq.) of phenyllithium solution in cyclohexane:diethyl ether 7:3 (1.3M) was added in one portion. The resulting dark solution was stirred 10 minutes and 2 mL of dry acetone was added. The mixture was stirred 10 minutes and additional 6 mL of acetone was added. After 5 minutes water (10 g) and NH$_4$Cl (10 g) was added. The mixture was filtered, concentrated, and the residue was purified by flash chromatography (ethyl acetate). Yield: 0.3 g of unreacted substrate 1-phenylphospholane-1-oxide (4%) and 8.2 g (86%) of trans-2-(1-hydroxy-1-methyl-ethyl)-1-phenylphospholane 1-oxide as white crystals; mp 112–114° C. (ethyl acetate); $^1$H NMR (500 MHz) δ: 1.17 (s, 3H), 1.27 (s, 3H), 1.53–1.68 (m, 1H), 1.85–1.93 (m, 1H), 1.95–2.33 (m, 5H), 4.5 (b, 1H), 7.38–7.52 (m, 3H), 7.62–7.70 (m, 2H); −$^{13}$C NMR (126 MHz) δ: 23.2 (d, J=6.1), 27.0 (d, J=11.3), 29.1 (d, J=9.0), 30.6 (d, J=2.8), 31.4 (d, J=66.8), 50.6 (d, J=66.5), 71.6 (d, J=3.9), 128.8 (d, J=11.6), 129.8 (d, J=9.8), 131.8 (d, J=2.9), 134.5 (d, J=87.7); $^{31}$P NMR (81 MHz) δ: 61.2; EI MS m/z (%): 223 (61), 220 (14), 203 (23), 181 (11), 180 (100), 179 (29), 160 (14), 152 (57), 141 (12), 132 (22), 105 (19), 104 (35), 81 (12), 77 (15), 55 (13), 47 (21), 43 (13), 41 (13); Elemental Anal. Calcd. for $C_{13}H_{19}O_2P$: C, 65.53; H, 8.04; found C, 65.10; H, 8.20.

Step 2

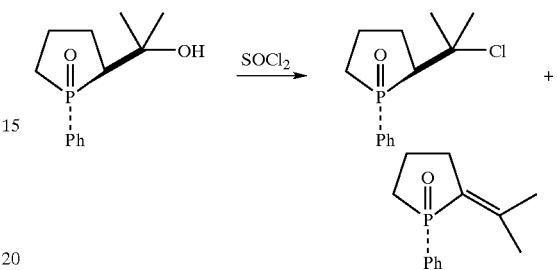

The same procedure as described in Example 2 was employed, but with trans-2-(1-hydroxy-1-methyl-ethyl)-1-phenylphospholane 1-oxide as a substrate, yielded: 36% of trans-2-(1-chloro-1-methyl-ethyl)-1-phenylphospholane 1-oxide as a colorless oil; $^1$H NMR (500 MHz) δ: 1.68 (s, 3H), 1.69–1.79 (m, 1H), 1.85 (s, 3H), 2.13–2.38 (m, 4H), 2.38–2.52 (m, 2H), 7.47–7.57 (m, 3H), 7.69–7.77 (m, 2H); $^{13}$C NMR (126 MHz) δ: 22.5 (d, J=3.7), 28.8 (d, J=11.4), 30.0 (d, J=1.5), 31.9 (d, J=67.5), 33.0 (d, J=1.9), 55.6 (d, J=62.3), 72.0 (d, J=2.6), 128.8 (d, J=11.7), 130.0 (d, J=9.6), 131.9 (d, J=2.9), 134.1 (d, J=90.9); $^{31}$P NMR (81 MHz) δ: 54.2; EI MS m/z (%): 222 (14), 221 (100), 220 (14), 125 (11), 95 (21), 77 (10), 47 (16), 41 (10); LSIMS(+) MS m/z: 257 (100, (M+H)$^+$), 221 (70); HR LSIMS(+) MS calcd. for $C_{13}H_{19}OPCl$: 257.0862, found 257.0855; and 51% of 2-isopropylidene-1-phenylphospholane 1-oxide as a colorless oil; $^1$H NMR (500 MHz) δ: 1.80 (d, J=2.2), 1.83 (d, J=1.6), 1.84–1.93 (m, 1H), 2.02–2.16 (m, 3H), 2.43–2.54 (m, 1H), 2.61–2.73 (m, 1H), 7.39–7.50 (m, 3H), 7.66–7.73 (m, 2H), $^{13}$C NMR (126 MHz) δ: 20.9 (d, J=6.1), 22.9 (d, J=12.5), 23.4 (d, J=8.6) (d, J=27.4), 31.1 (d, J=72.2), 128.0 (d, J=98.2), 128.5 (d, J=11.7), 130.4 (d, J=10.3), 131.3 (d, J=2.8), 134.4 (d, J=94.4), 148.5 (d, J=8.4); $^{31}$P NMR (162 MHz) δ: 46.8; EI MS m/z (%): 221 (14), 220 (98, M$^+$), 219 (100), 205 (18), 192 (21), 191 (12), 143 (11), 125 (20), 77 (13), 67 (10), 47 (28), 41 (12); HR MS calcd. for $C_{13}H_{17}OP$: 220.1017, found 220.1010.

Recycling of trans-2-(1-chloro-1-methyl-ethyl)-1-phenylphospholane 1-oxide and its transformation into 2-isopropylidene-1-phenylphospholane 1-oxide using the same procedure as described in Example 2 with DBU increased the total yield of 2-isopropylidene-1-phenylphospholane 1-oxide to yield 67%.

Step 3

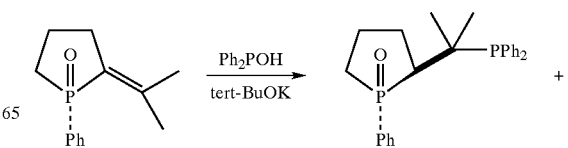

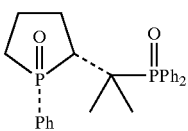

In a 100 mL round bottom 2-neck flask charged with a magnetic stirring bar 140 mg (0.64 mmol) of 2-isopropylidene-1-phenylphospholane 1-oxide and 138 mg (1.5 eq.) of diphenylphosphine oxide were dissolved in 40 mL of dry THF. 110 mg (2 eq.) of potassium tert-butoxide was added and the reaction was stirred four hours. Additional 138 mg of diphenylphosphine oxide and 110 mg of tert-BuOK were added and the stirring was continued at rt overnight. Next 200 mL of water was added and the mixture was extracted with chloroform (4×50 mL). Combined organic phases were dried over MgSO$_4$, concentrated and purified by chromatography (ethyl acetate:methanol 10:1). Yield: 33% of substrate 2-isopropylidene-1-phenylphospholane 1-oxide, 8 mg (3%) of trans-2-(1-diphenylphosphinoyl-1-methyl-ethyl)-1-phenylphospholane 1-oxide as a colorless oil; $^1$H NMR (500 MHz) δ: 1.26 (d, J=16.6, 3H), 1.35–1.53 (m, 1H), 1.73 (d, J=16.0), 1.81–2.26 (m, 5H), 2.26–2.47 (m, 1H), 7.38–7.55 (m, 10H), 7.55–7.63 (m, 1H), 7.64–7.79 (m, 1H), 7.86–7.97 (m, 3H); $^{31}$P NMR (162 MHz) δ: 37.7 (d, J=47.4), 58.5 (d, J=47.4); EI MS m/z (%): 422 (7, M$^+$), 222 (15), 221 (100), 55 (13), 53 (11), 51 (30); HR MS calcd. for $C_{25}H_{28}O_2P_2$: 422.1565, found 422.1561; and 200 mg (64%) of cis-2-(1-diphenylphosphinoyl-1-methyl-ethyl)-1-phenylphospholane 1-oxide as white powder; mp 143–146° C. (hexane); $^1$H NMR (500 MHz) δ: 0.68 (d, J=15.3, 3H), 1.13–1.28 (m, 1H), 1.40 (d, J=17.1, 3H), 1.59–1.80 (m, 2H), 1.87–2.09 (m, 3H), 2.38–2.63 (m, 1H), 7.28–7.53 (m, 9H), 7.68–7.82 (m, 4H), 7.95–8.03 (m, 2H); $^{13}$C NMR (126 MHz) δ: 17.3, 21.0 (d, J=3.2), 23.8 (d, J=4.4), 26.8 (d, J=68.9), 27.3 (d, J=14.3), 38.3 (dd, J=1.6, J=67.2), 50.1 (d, J=61.3), 128.1 (d, J=10.9), 128.6 (d, J=11.1), 128.7 (d, J=10.7), 130.3 (d, J=89.1), 131.4 (d, J=2.7), 131.7 (d, J=9.2), 131.9 (d, J=2.53), 132.1 (d, J=7.8), 132.3 (d, J=8.0), 134.7 (d, J=87.7); $^{31}$P NMR (202 MHz) δ: 40.0 (d, J=48.8), 57.4 (d, J=48.8); EI MS m/z (%): 422 (7, M$^+$), 244 (13), 222 (14), 221 (100), Elemental Anal. Calcd. for $C_{25}H_{28}O_2P_2$: C, 71.08; H, 6.68; found C, 70.85; H, 6.74.

EXAMPLE 13a

Preparation of [(η-1,2,5,6)-1,5-Cyclooctadiene][(1R,2R)-cis-1-phenyl-2-[(diphenylphosphino-κP)methyl]phospholane-κP]rhodium(1+) hexafluoroantimonate {[Rh((R,R)-cis-PMP5)(cod)]SbF$_6$}

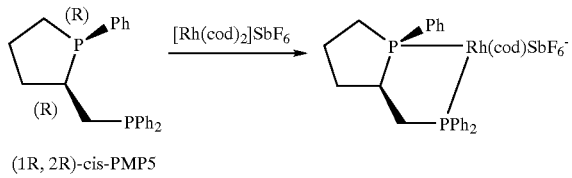

(1R, 2R)-cis-PMP5

In a 100 ml round bottom 2-neck flask flushed with argon and equipped with a magnetic stirring bar 166.56 mg Rh(cod)$_2$SbF$_6$ was dissolved in 100 ml dry THF. The mixture was cooled to −80° C. and a solution of 108.60 mg (1R,2R)-cis-1-phenyl-2-[(diphenylphosphino)methyl] phospholane {(R,R)-cis-PMP5} in 50 ml THF was added dropwise. The mixture was allowed to warm to room temperature, the solvent was evaporated and the residue was dissolved in THF/CH$_2$Cl$_2$ (1:1). A few drops of hexane were added to render the solution turbid, then a few drops of methanol were added. Again a few drops of hexane were added. Overnight an orange-yellow precipitate formed which was filtered and washed with hexane. Yield 194.76 mg (80%) of [(η-1,2,5,6)-1,5-cyclooctadiene][(1R,2R)-cis-1-phenyl-2-[(diphenylphosphino-κP)methyl]phospholane-κP]rhodium(1+) hexafluoroantimonate as an orange solid. $^{31}$P NMR (300 MHz) δ: 50.6 (dd, J=26.7, J=148.5), 70.8 (dd, J=26.7, J=146.3).

EXAMPLE 13b

Preparation of [(η-1,2,5,6)-1,5-Cyclooctadiene][(1S, 2S)-cis-1-phenyl-2-[(diphenyl-phosphino-κP) methyl]phospholane-κP]rhodium(1+) hexafluoroantimonate {[Rh((S,S)-cis-PMP5)(cod)] SbF$_6$}

The complex [(η-1,2,5,6)-1,5-cyclooctadiene][(1S,2S)-cis-1-phenyl-2-[(diphenylphosphino-κP)methyl] phospholane-κP]rhodium(1+) hexafluoroantimonate was prepared analogously to Example 9a) starting from (1S,2S)-cis-1-phenyl-2-[(diphenylphosphino)methyl]phospholane {(S,S)-cis-PMP5}.

EXAMPLE 13c

Preparation of [(η-1,2,5,6)-1,5-Cyclooctadiene][(1R,2S)-1-phenyl-2-(diphenylphosphino-κP)methyl]phospholane-κP]rhodium(1+) hexafluoroantimonate {[Rh((R,S)-trans-PMP5)(cod)]SbF$_6$}

The complex [(η-1,2,5,6)-1,5-cyclooctadiene][(1R,2S)-trans-1-phenyl-2-[(diphenylphosphino-κP)methyl] phospholane-κP]rhodium(1+) hexafluoroantimonate which was needed for comparison experiments was prepared analogously to Example 9a) starting from (1R,2S)-trans-1-phenyl-2-[(diphenylphosphino)methyl]phospholane {(R,S)-trans-PMP5} red solid, yield 88%; $^{31}$P NMR (300 MHz) δ: 56.5 (dd, J=26.7, J=147.0), 74.8 (dd, J=26.7, J=145.5).

EXAMPLES OF HYDROGENATIONS

The hydrogenation examples were carried out as follows: In a dry box, an autoclave with a 20 ml glass tube insert was charged with a magnetic stirring bar, the hydrogenation substrate (1 mmol), anhydrous degassed methanol (7 ml) and the metal complex pre-catalyst (0.81 mg, 0.001 mmol).

After 5 cycles of evacuation/filing with hydrogen, the autoclave was pressurized to an initial pressure of 150 kPa. The reaction was stirred at room temperature for 2 h. The reaction mixture was concentrated and the residue was analyzed by GC.

Preferably, the metal complex pre-catalyst was prepared as described in Example 9 and used in its isolated form for the hydrogenation. Alternatively, the complex may be prepared in situ, as described in Example H.

Example A

Hydrogenation of 2-acetylamino-acrylic acid methyl ester and 2-acetylamino-acrylic acid, respectively, using an isolated pre-catalyst [Rh(Ligand)(cod)]SbF$_6$ (with cis-PMP5 or trans-PMP5 as the Ligand). The hydrogenation was carried out in methanol (MeOH) at room temperature at an initial H$_2$ pressure as indicated in table A:

TABLE A

| Substrate | Ligand | Initial $H_2$ pressure kPa | Time (h) | S/C | % conv.[1] | % ee[2] |
|---|---|---|---|---|---|---|
| 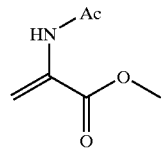 | (R,R)-cis-PMP5 | 150 | 2 | 1000 | 100 | 94 (S) |
| | (R,S)-trans-PMP5 | 150 | 2 | 1000 | 100 | 33 (S) |
| | (R,R)-cis-PMP5 | 500 | 16 | 1000 | 100 | 91 (S) |
| | (R,R)-cis-PMP5 | 500 | 3 | 100 | 100 | 93 (S) |
| 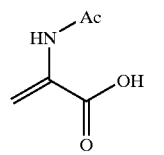 | (R,R)-cis-PMP5 | 150 | 2 | 1000 | 100 | 85 (S) |
| | (R,S)-trans-PMP5 | 150 | 2 | 1000 | 100 | 16 (S) |
| | (R,R)-cis-PMP5 | 500 | 16 | 1000 | 100 | 82 (S) |
| | (R,R)-cis-PMP5 | 500 | 3 | 100 | 100 | 84 (S) |

[1] Determined by GC [area-%].
[2] Determined by GC on a chiral column.

Example B

The hydrogenation of 2-methylene-succinic acid and 2-methylene-succinic acid dimethyl ester, respectively, with isolated pre-catalysts [Rh(Ligand)(cod)]$SbF_6$ (with cis-PMP5 or trans-PMP5 as the Ligand) was carried out in methanol (MeOH) at room temperature at an initial $H_2$ pressure as indicated in table B:

TABLE B

| Substrate | Ligand | Initial $H_2$ pressure kPa | Time (h) | S/C | % conv.[1] | % ee[2] |
|---|---|---|---|---|---|---|
| 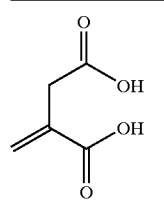 | (R,R)-cis-PMP5 | 150 | 2 | 1000 | 99.8 | 97 (R) |
| | (R,S)-trans-PMP5 | 150 | 2 | 1000 | 100 | 68 (R) |
| | (R,R)-cis-PMP5 | 500 | 16 | 1000 | 100 | 96 (R) |
| | (R,R)-cis-PMP5 | 500 | 3 | 100 | 100 | 97 (R) |
| 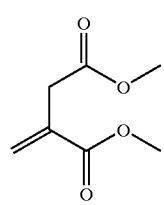 | (R,R)-cis-PMP5 | 150 | 2 | 1000 | 77 | 91 (R) |
| | (R,S)-trans-PMP5 | 150 | 2 | 1000 | 100 | 62 (R) |
| | (R,R)-cis-PMP5 | 500 | 16 | 1000 | 100 | 89 (R) |
| | (R,R)-cis-PMP5 | 500 | 3 | 100 | 100 | 90 (R) |

[1] Determined by GC [area-%].
[2] Determined by GC on a chiral column.

Example C

The hydrogenation of 2-acetylamino-3-phenyl acrylic acid and 2-acetylamino-3-phenyl acrylic acid triethylammonium salt, respectively, was carried out with 0.1 mol % isolated pre-catalysts [Rh(Ligand)(cod)]$SbF_6$ with cis-PMP5 or trans-PMP5 as the Ligand in methanol (MeOH) at room temperature at an initial $H_2$ pressure as indicated in table C:

TABLE C

| Substrate | Ligand | Initial H$_2$ pressure kPa | Time (h) | S/C | % conv.[1] | % ee[2] |
|---|---|---|---|---|---|---|
| 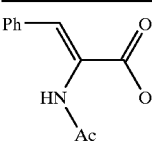 | (R,R)-cis-PMP5 | 150 | 2 | 1000 | 75 | 98 (S) |
| | (R,R)-cis-PMP5 | 150 | 16 | 1000 | 100 | 98 (S) |
| | (R,S)-trans-PMP5 | 150 | 2 | 1000 | 100 | 25 (R) |
| | (R,R)-cis-PMP5 | 500 | 16 | 1000 | 100 | 96 (S) |
| | (R,R)-cis-PMP5 | 500 | 3 | 100 | 100 | 97 (S) |
| 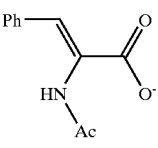 | (R,R)-cis-PMP5 | 150 | 16 | 1000 | 78 | 98 (S) |
| | (R,S)-trans-PMP5 | 150 | 16 | 1000 | 100 | 48 (S) |
| | (R,R)-cis-PMP5 | 500 | 3 | 1000 | 57 | 98 (S) |

[1] Determined by GC [area-%]
[2] Determined by GC on a chiral column.

Example D

The hydrogenation of the 2-acetylamino-acrylic acid triethylammonium salt, the 2-methylene-succinic acid and of 2-methylene-succinic acid bis(triethylammonium) salt, respectively, was carried out with 0.1 mol % isolated pre-catalysts [Rh(Ligand)(cod)]SbF$_6$ (with cis-PMP5 or trans-PMP5 as the Ligand) in methanol (MeOH) at room temperature at an initial H$_2$ pressure as indicated in table D:

Example E

The hydrogenation of the 2-acetyloxy-acrylic acid ethyl ester was carried out with 0.1 mol % isolated pre-catalysts [Rh(Ligand)(cod)]SbF$_6$ (with cis-PMP5 or trans-PMP5 or Prophos as the Ligand) in methanol (MeOH) at room temperature at an initial H$_2$ pressure as indicated in table E:

TABLE D

| Substrate | Ligand | Initial H$_2$ pressure | Time (h) | S/C | % conv.[1] | % ee[2] |
|---|---|---|---|---|---|---|
| 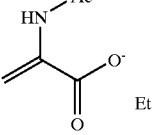 | (R,R)-cis-PMP5 | 1.5 | 2 | 1000 | 100 | 96 (S) |
| | (R,S)-trans-PMP5 | 1.5 | 2 | 1000 | 99 | 57 (S) |
| | (R,R)-cis-PMP5 | 5 | 3 | 1000 | 100 | 96 (R) |
| 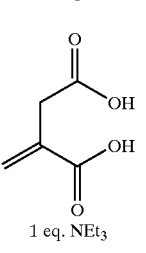 | (R,R)-cis-PMP5 | 1.5 | 2 | 1000 | 99.9 | 98 (R) |
| | (R,S)-trans-PMP5 | 1.5 | 2 | 1000 | 100 | 77 (R) |
| | (R,R)-cis-PMP5 | 5 | 16 | 1000 | 100 | 96 (R) |
| | (R,R)-cis-PMP5 | 1.5 | 2 | 1000 | 90 | 96 (R) |
| | (R,S)-trans-PMP5 | 1.5 | 2 | 1000 | 100 | 85 (R) |

[1] Determined by GC [area-%].
[2] Determined by GC on a chiral column.

TABLE E

| Substrate | Ligand | Initial H$_2$ kPa | Time (h) | S/C | % conv.[1] | % ee[2] |
|---|---|---|---|---|---|---|
| 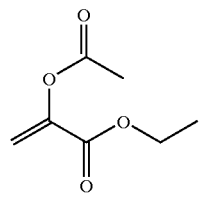 | (R)-Prophos | 500 | 3 | 100 | 100 | 78 (S) |
| | (R,R)-cis-PMP5 | 150 | 2 | 1000 | 33 | 95 (S) |
| | (R,S)-trans-PMP5 | 150 | 2 | 1000 | 35 | 23 (S) |
| | (R,R)-cis-PMP5 | 500 | 3 | 100 | 100 | 97 (S) |
| | (R,R)-cis-PMP5 | 500 | 16 | 1000 | 100 | 97 (S) |
| | (R,R)-cis-PMP5 | 500 | 16 | 10 000 | 45 | 97 (S) |

[1] Determined by GC [area-%],
[2] Determined by GC on a chiral column.

Example F

The hydrogenation of the oxo-phenylacetic acid methyl ester, oxo-phenylacetic acid and oxo-phenylacetic acid triethylammonium salt, respectively, was carried out with 0.1 mol % isolated pre-catalysts [Rh(Ligand)(cod)]SbF$_6$ (with cis-PMP5 or trans-PMP5 as the Ligand) in methanol (MeOH) at room temperature at an initial H$_2$ pressure of 4000 kPa for 4 h. The results are shown in table F:

TABLE F

| Substrate | Ligand | % conversion[1] | % ee[2] |
|---|---|---|---|
| 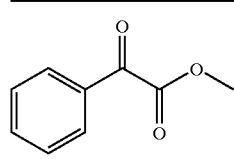 | (R,R)-cis-PMP5 | 8 | 2 |
| | (R,S)-trans-PMP5 | 4 | 3 |
| 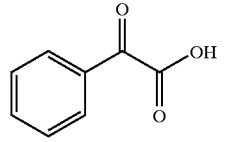 | (R,R)-cis-PMP5 | 80 | 3 |
| | (R,S)-trans-PMP5 | 3 | 5 |
| 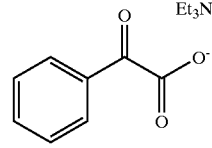 | (R,R)-cis-PMP5 | 98 | 9 |
| | (R,S)-trans-PMP5 | 36 | 3 |

[1] Determined by GC [area-%].
[2] Determined by GC on a chiral column.

Example G

The hydrogenation of N-(1-phenylvinyl)acetamide and acetic acid 1-phenylvinyl ester, respectively, was carried out with isolated pre-catalysts [Rh(Ligand)(cod)]SbF$_6$ (with cis-PMP5 or trans-PMP5 as the Ligand) in methanol (MeOH) at room temperature at an initial H$_2$ pressure as mentioned in table G:

TABLE G

| Substrate | Ligand | Initial H$_2$ kPa | Time (h) | S/C | % convers.[1] | % ee[2] |
|---|---|---|---|---|---|---|
| 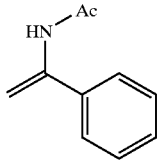 | (R,R)-cis-PMP5 | 150 | 6 | 500 | 100 | 10 |
| | (R,S)-trans-PMP5 | 150 | 6 | 500 | 100 | 20 |
| | (R,R)-cis-PMP5 | 150 | 6 | 500 | 100 | 10 |
| 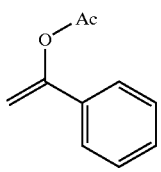 | (R,R)-cis-PMP5 | 150 | 7 | 1000 | 21 | 22 |
| | (R,S)-trans-PMP5 | 150 | 7 | 1000 | 13 | 22 |
| | (R,R)-cis-PMP5 | 1500 | 7 | 1000 | 78 | 18 |

[1] Determined by GC [area-%].
[2] Determined by GC on a chiral column.

Example H

Using a Cationic Catalysts Prepared in situ

In this example the metal complex was prepared in situ by dissolving of 0.010 mmol rhodium precursor $(Rh(cod)_2X)$ and 0.011 mmol ligand in 4 ml of methanol. The orange solution was stirred 45 minutes and then mixed with a solution of 1 mmol of substrate dissolved in 3 ml of methanol. Procedure of hydrogenation was carried out as described above catalytic hydrogenation of 2-acetylamino-acrylic acid methyl ester was carried out at room temperature with an initial $H_2$ pressure of 500 kPa, 3 h, S/C 100. The ligands X were

| Substrate | Ligand | X | Solvent | % conv.[1] | % ee[2] |
|---|---|---|---|---|---|
| 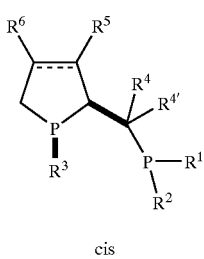 | (S,S)-cis-PMP5 | BARF | MeOH | 100 | 81 (R) |
| | (S,S)-cis-PMP5 | $PF_6$ | MeOH | 100 | 82 (R) |
| | (S,R)-trans-PMP5 | $PF_6$ | MeOH | 100 | 5 (R) |

[1] Determined by GC [area-%].
[2] Determined by GC on a chiral column.

What is claimed is:

1. A phosphine compound of the formula I

I cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is an optional double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I.

2. The compound of formula I according to claim 1 wherein
- $R^1$ and $R^2$ are the same and are alkyl, aryl, cycloalkyl or heteroaryl, said alkyl, aryl, cycloalkyl or heteroaryl may be substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
- $R^3$ is alkyl or aryl;
- $R^{4'}$ and $R^4$ are hydrogen;
- $R^5$ and $R^6$ are independently of each other hydrogen, $C_1$–$C_3$-alkyl or phenyl; the dotted line is absent;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I.

3. The compound of formula I according to claim 1, wherein
- $R^1$ and $R^2$ are the same and are aryl;
- $R^3$ is tert.-butyl or phenyl;
- $R^{4'}$ and $R^4$ are the same and are hydrogen;
- $R^5$ and $R^6$ are hydrogen; and the dotted line is absent.

4. The compound of formula I according to claim 1, wherein
- $R^1$ and $R^2$ are the same and are alkyl;
- $R^3$ is tert.-butyl or phenyl;
- $R^{4'}$ and $R^4$ are the same and are hydrogen;
- $R^5$ and $R^6$ are hydrogen; and the dotted line is absent.

5. The compound of formula I according to claim 1, wherein
- $R^1$ and $R^2$ are the same and are cycloalkyl;
- $R^3$ is tert.-butyl or phenyl;
- $R^{4'}$ and $R^4$ are the same and are hydrogen;
- $R^5$ and $R^6$ are hydrogen; and the dotted line is absent.

6. The compound of formula I according to claim 1, wherein
- $R^1$ and $R^2$ are the same and are heteroaryl;
- $R^3$ is tert.-butyl or phenyl;
- $R^{4'}$ and $R^4$ are the same and are hydrogen;
- $R^5$ and $R^6$ are hydrogen; and the dotted line is absent.

7. The compound of formula I, wherein $R^1$ and $R^2$ are the same and are phenyl, $R^3$ is phenyl and $R^4$, $R^{4'}$, $R^5$ and $R^6$ are hydrogen.

8. A transition metal complex of formula II $$M_mL_nX_pA_q$$ II wherein

M is a transition metal,

L is the diphosphine compound of formula I

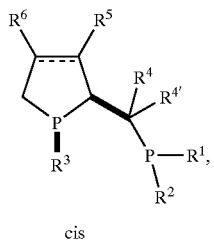

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is an optional double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I;

X is a coordinating anion, m, n and p are each 1, and q is 0, if M is Rh.

9. A transition metal complex of formula II

 $M_mL_nX_pA_q$     II wherein

M is a transition metal,

L is the diphosphine compound of formula I

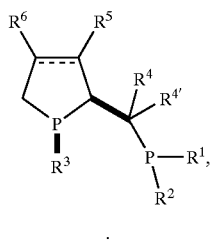

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is an optional double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is acyloxy, m and n are each 1, p is 2, and q is 0, if M is Ru.

10. A transition metal complex of formula II

 $M_mL_nX_pA_q$     II wherein

M is a transition metal,

L is the diphosphine compound of formula I

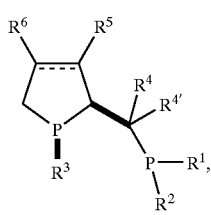

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is Cl, m and n are each 2, p is 4, q is 1, and A is triethylamine, if M is Ru.

11. A transition metal complex of formula II $$M_mL_nX_pA_q \qquad \text{II}$$

wherein

M is a transition metal,

L is the diphosphine compound of formula I

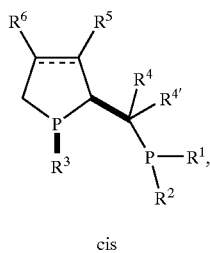

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is a π-methallyl group, m and n are each 1, p is 2, and q is 0, if M is Ru.

12. A transition metal complex of formula II $$M_mL_nX_pA_q \qquad \text{II}$$

wherein

M is a transition metal,

L is the diphosphine compound of formula I

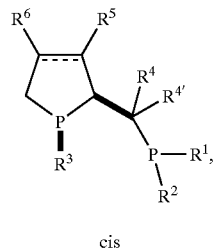

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is a coordinating anion, m, n and p are each 1, and q is 0, if M is Ir.

13. A transition metal complex of formula II $$M_mL_nX_pA_q \qquad \text{II}$$

wherein

M is a transition metal,

L is the diphosphine compound of formula I wherein

R$^1$ and R$^2$ are independently of each other unsubstituted alkyl, aryl, cycloalkyl or heteroaryl, or alkyl, aryl, cydoalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is Cl, m and n are each 1, p is 2, and q is 0, if M is Pd.

14. A transition metal complex of formula II $$M_mL_nX_pA_q \qquad \text{II}$$

wherein

M is a transition metal,

L is the diphosphine compound of formula I

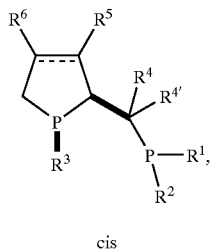

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is Cl, Br or I, m and n are each 1, p is 2, and q is 0, if M is Ni.

15. A transition metal complex of formula $$M_mL_nX_pA_q \qquad \text{II}$$

wherein

M is Rh,

L is the diphosphine compound the formula I

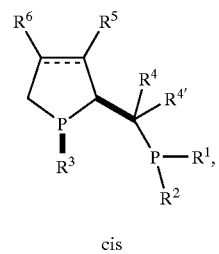

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is a coordinating anion, m, n and p are each 1, and q is 0.

16. A metal complex of formula $$[M_mL_nX_pA_q]D_r \qquad \text{III}$$

wherein

M is a transition metal,

L is the diphosphine compound of the formula I

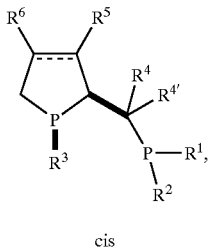

cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is optionally a double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I,
- X is a diene ligand,
- D is a non-coordinating anion,
- m, n, p and r are each 1, and
- q is 0, if M is Rh.

17. A metal complex of formula $$[M_mL_nX_pA_q]D_r \qquad III$$

wherein
M is for a transition metal,
L is the diphosphine compound of formula I

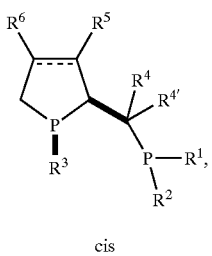

cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is optionally a double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I,
- X is an olefinic ligand,
- D is a non-coordinating anion,
- m, n and r are each 1,
- p is 2 and
- q is 0, if M is Rh.

18. A metal complex of formula $$[M_mL_nX_pA_q]D_r \qquad III$$

wherein
M is a transition metal,
L is the diphosphine compound of the formula I

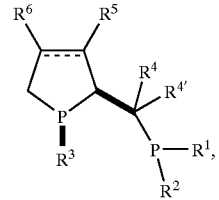

cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, $-SO_2-R^7$, $-SO_3^-$, $-CO-NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is optionally a double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I, X is Cl, Br or I, A is benzene or p-cymene, D is Cl, Br or I, and m, n, p, q and r are each 1, if M is Ru.

19. A metal complex of formula $$[M_mL_nX_pA_q]D_r \quad \text{III}$$

wherein

M is for a transition metal,

L is for the diphosphine compound of formula I

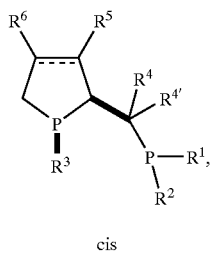

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the pospholane phophorus atom and the substituent on the C2 atom of the phospholane ring are in cis relation to each other as indicated by the bold bonds in formula I, D is a non-coordinating anion, m and n are each 1, p and q are each 0, and r is 2, if M is Ru.

20. A metal complex of formula $$[M_mL_nX_pA_q]D_r \quad \text{III}$$

wherein

M is for a transition metal,

L is for the diphosphine compound of the formula I

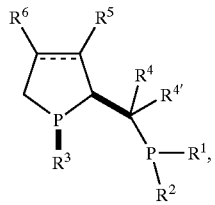

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the pospholane phophorus atom and the substituent on the C2 atom of the phospholane ring are in cis relation to each other as indicated by the bold bonds in formula I, X is a diene ligand, D is a non-coordinating anion, m, n, p and r are each 1, and q is 0, if M is Ir.

21. A metal complex of formula $$[M_mL_nX_pA_q]D_r \quad \text{III}$$

wherein

M is for a transition metal,

L is the diphosphine compound of the formula I

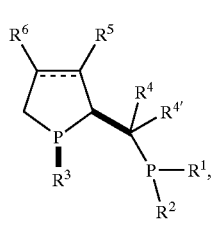

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3$$^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is an olefinic ligand, D is a non-coordinating anion, m, p and r are each 1, n is 2 and q is 0, if M is Ir.

22. A metal complex of formula

[M$_m$L$_n$X$_p$A$_q$]D$_r$    III wherein

M is a transition metal,

L is the diphosphine compound of formula I

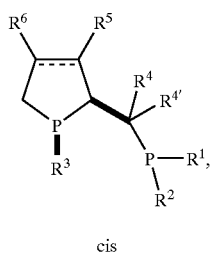

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3$$^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, X is a π-allyl group, D is a non-coordinating anion, m, n, p and r are each 1, and q is 0, if M is Pd.

23. A metal complex of formula

[M$_m$L$_n$X$_p$A$_q$]D$_r$    III wherein

M is for Rh,

L is for the diphosphine compound of the formula I

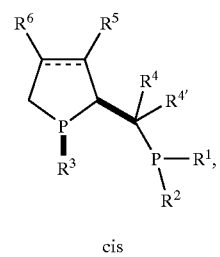

cis wherein

R$^1$ and R$^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3$$^-$, —CO—NR$^8$R$^{8'}$, carboxy, alkoxycarbonyl, trialkylsilyl, diarylalkylsilyl, dialkylarylsilyl or triarylsilyl;

R$^3$ is alkyl, cycloalkyl, aryl or heteroaryl;

R$^{4'}$ and R$^4$ is independently of each other hydrogen, alkyl or optionally substituted aryl; or R$^{4'}$ and R$^4$ together, with the C-atom they are attached, form a 3–8-membered carbocyclic ring;

dotted line is optionally a double bond;

R$^5$ and R$^6$ are independently of each other hydrogen, alkyl or aryl;

R$^7$ is alkyl, aryl or NR$^8$R$^{8'}$; and

R$^8$ and R$^{8'}$ are independently of each other hydrogen, alkyl or aryl;

the substituents R$^3$ on the phospholane phophorus atom and the substituent on the C2 atom of the phospholane ring are in cis relation to each other as indicated by the bold bonds in formula I, and wherein X is a diene ligand, D is a non-coordinating anion, m, n, p and r are each 1, and q is 0.

24. A metal complex of formula

[M$_m$L$_n$X$_p$A$_q$]D$_r$    III wherein

M is for Rh,

45

L is for the diphosphine compound of the formula I

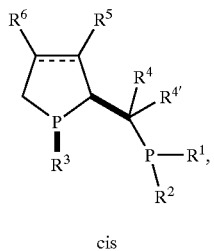

cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —$SO_2$—$R^7$, —$SO_3^-$, —CO—$NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is optionally a double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I,
- X is an olefinic ligand,
- D is a non-coordinating anion,
- m, n and r are each 1,
- p is 2 and
- q is 0.

25. An optical active compound of formula 6

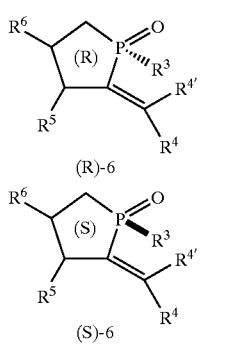

wherein $R^{4'}$ and $R^4$ is independently of each other hydrogen, alkyl or optionally substituted aryl; or
  $R^{4'}$ and $R^4$ together, with the C-atom they are attached, form a 3–8-membered carbocyclic ring;
  dotted line is absent or is present and forms a double bond;

46

$R^5$ and $R^6$ are independently of each other hydrogen, alkyl or aryl.

26. A process for the asymmetric hydrogenation of a prochiral olefinic or ketonic compound wherein the reaction is carried out in presence of metal complex of fomula II $$M_mL_nX_pA_q \qquad \text{II}$$

wherein
M is a transition metal,
L is the diphosphine compound of the formula I

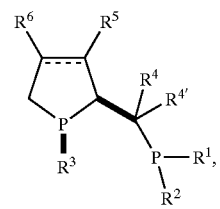

cis wherein
- $R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —$SO_2$—$R^7$, —$SO_3^-$, —CO—$NR^8R^{8'}$, carboxy, alkoxycarbonyl, trialkylsilyl, diarylalkylsilyl, dialkylarylsilyl or triarylsilyl;
- $R^3$ is alkyl, cycloalkyl, aryl or heteroaryl;
- $R^{4'}$ and $R^4$ is independently of each other hydrogen, alkyl or optionally substituted aryl; or
- $R^{4'}$ and $R^4$ together, with the C-atom they are attached, form a 3–8-membered carbocyclic ring;
- dotted line is optionally a double bond;
- $R^5$ and $R^6$ are independently of each other hydrogen, alkyl or aryl;
- $R^7$ is alkyl, aryl or $NR^8R^{8'}$; and
- $R^8$ and $R^{8'}$ are independently of each other hydrogen, alkyl or aryl;
- the substituents $R^3$ on the phospholane phophorus atom and the substituent on the C2 atom of the phospholane ring are in cis relation to each other as indicated by the bold bonds in formula I,
- X is a coordinating anion,
- m, n and p are each 1, and
- q is 0, if M is Rh, or wherein
M is a transition metal,
L is the diphosphine compound of formula I,
X is acyloxy,
m and n are each 1,
p is 2, and
q is 0, if M is Ru, or wherein
M is a transition metal,
L is the diphosphine compound of formula I,
X is Cl,
m and n are each 2,
p is 4, q is 1, and  
A is triethylamine, if M is Ru, or  
wherein  
M is a transition metal,  
L is the diphosphine compound of formula I,  
X is a π-methallyl group,  
m and n are each 1,  
p is 2, and  
q is 0, if M is Ru, or  
wherein  
M is a transition metal,  
L is the diphosphine compound of formula I,  
X is a coordinating anion,  
m, n and p are each 1, and  
q is 0, if M is Ir, or  
wherein  
M is a transition metal,  
L is the diphosphine compound of formula I,  
X is Cl,  
m and n are each 1,  
p is 2, and  
q is 0, if M is Pd, or  
wherein  
M is a transition metal,  
L is the diphosphine compound of formula I,  
X is Cl, Br or I,  
m and n are each 1,  
p is 2, and  
q is 0, if M is Ni, or  
wherein  
M is Rh,  
L is the diphosphine compound of formula I;  
X is a coordinating anion,  
m, n and p are each 1, and  
q is 0.

27. A process for the asymmetric hydrogenation of a prochiral olefinic or ketonic compound wherein the reaction is carried out in presence of metal complex of formula III $$[M_m L_n X_p A_q] D_r \qquad \text{III}$$

wherein  
M is a transition metal,  
L is the diphosphine compound of the formula I

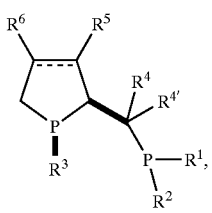

cis wherein  
$R^1$ and $R^2$ are independently of each other unsubstituted alkyl, aryl, cycloalkyl or heteroaryl, or alkyl, aryl, cycloalkyl or heteroaryl each of which independently is substituted by alkyl, alkoxy, halogen, hydroxy, amino, mono- or dialkylamino, aryl, —SO$_2$—R$^7$, —SO$_3^-$, —CO—NR$^8$R$^{8'}$, carboxy, alkoxycarbonyl, trialkylsilyl, diarylalkylsilyl, dialkylarylsilyl or triarylsilyl;  
$R^3$ is alkyl, cycloalkyl, aryl or heteroaryl;  
$R^{4'}$ and $R^4$ is independently of each other hydrogen, alkyl or optionally substituted aryl; or  
$R^{4'}$ and $R^4$ together, with the C-atom they are attached, form a 3–8-membered carbocyclic ring;  
dotted line is optionally a double bond;  
$R^5$ and $R^6$ are independently of each other hydrogen, alkyl or aryl;  
$R^7$ is alkyl, aryl or NR$^8$R$^{8'}$; and  
$R^8$ and $R^{8'}$ are independently of each other hydrogen, alkyl or aryl;  
the substituents $R^3$ on the pholpholane phophorus atom and the substituent on the C2 atom of the phospholane ring are in cis relation to each other as indicated by the bold bonds in formula I,  
X is a diene ligand,  
D is a non-coordinating anion,  
m, n, p and r are each 1, and  
q is 0, if M is Rh, or  
wherein  
M is for a transition metal,  
L is the diphosphine compound of formula I,  
X is an olefinic ligand,  
D is a non-coordinating anion,  
m, n and r are each 1,  
p is 2 and  
q is 0, if M is Rh, or  
wherein  
M is a transition metal,  
L is the diphosphine compound of formula I;  
X is Cl, Br or I,  
A is benzene or p-cymene,  
D is Cl, Br or I, and  
m, n, p, q and r are each 1, if M is Ru, or  
wherein  
M is for a transition metal,  
L is for the diphosphine compound of formula I,  
D is a non-coordinating anion,  
m and n are each 1,  
p and q are each 0, and  
r is 2, if M is Ru, or  
wherein  
M is for a transition metal,  
L is for the diphosphine compound of formula I,  
X is a diene ligand,  
D is a non-coordinating anion,  
m, n, p and r are each 1, and  
q is 0, if M is Ir, or  
wherein  
M is for a transition metal,  
L is the diphosphine compound of formula I,  
X is an olefinic ligand,  
D is a non-coordinating anion,  
m, p and r are each 1,  
n is 2 and  
q is 0, if M is Ir, or wherein
- M is a transition metal,
- L is the diphosphine compound of formula I;
- X is a π-allyl group,
- D is a non-coordinating anion,
- m, n, p and r are each 1, and
- q is 0, if M is Pd, or wherein
- M is for Rh,
- L is for the diphosphine compound of formula I,
- X is a diene ligand,
- D is a non-coordinating anion,
- m, n, p and r are each 1, and
- q is 0, or wherein
- M is for Rh,
- L is for the diphosphine compound of formula I,
- X is an olefinic ligand,
- D is a non-coordinating anion,
- m, n and r are each 1,
- p is 2 and
- q is 0.

* * * * *

UNITED STATES PATENT AND TRADEMARK OFFICE
CERTIFICATE OF CORRECTION

PATENT NO. : 6,984,744 B2
APPLICATION NO. : 10/721038
DATED : January 10, 2006
INVENTOR(S) : Piotr Osinski et al.

It is certified that error appears in the above-identified patent and that said Letters Patent is hereby corrected as shown below:

Title page,
Item [73], Assignee, delete "Hoffman-La Roche Inc., Nutley, NJ (US)" and insert -- Hoffmann-La Roche Inc., Nutley, NJ (US) --.

Signed and Sealed this

Fourth Day of July, 2006

JON W. DUDAS
*Director of the United States Patent and Trademark Office*